(12) United States Patent
Levine

(10) Patent No.: US 9,622,741 B2
(45) Date of Patent: Apr. 18, 2017

(54) SURGICAL SUTURING DEVICE AND TOOLS USED THEREWITH

(75) Inventor: Marshall S. Levine, Wayne, PA (US)

(73) Assignee: ALPHA SCIENTIFIC CORPORATION, Malvern, PA (US)

( * ) Notice: Subject to any disclaimer, the term of this patent is extended or adjusted under 35 U.S.C. 154(b) by 506 days.

(21) Appl. No.: 12/452,743

(22) PCT Filed: Jul. 25, 2008

(86) PCT No.: PCT/US2008/009012
§ 371 (c)(1),
(2), (4) Date: Jan. 20, 2010

(87) PCT Pub. No.: WO2009/045248
PCT Pub. Date: Apr. 9, 2009

(65) Prior Publication Data
US 2010/0130991 A1    May 27, 2010

Related U.S. Application Data

(60) Provisional application No. 60/962,031, filed on Jul. 26, 2007.

(51) Int. Cl.
*A61B 17/04* (2006.01)
*A61B 17/06* (2006.01)
(Continued)

(52) U.S. Cl.
CPC ...... *A61B 17/0482* (2013.01); *A61B 17/0485* (2013.01); *A61B 17/06166* (2013.01);
(Continued)

(58) Field of Classification Search
CPC ............ A61B 17/0469; A61B 17/0482; A61B 17/0483; A61B 17/0682; A61B 17/282;
(Continued)

(56) References Cited

U.S. PATENT DOCUMENTS 669,034 A * 2/1901 Manly ........................... 606/118
755,921 A * 3/1904 O'Neill ......................... 606/148
(Continued)

FOREIGN PATENT DOCUMENTS

EP    1 598 017    11/2005
EP    1 862 125    12/2007
(Continued)

OTHER PUBLICATIONS

Office Action issued Jul. 31, 2014 in AU Application No. 2010232964.
(Continued)

*Primary Examiner* — Christopher L Templeton
(74) *Attorney, Agent, or Firm* — Panitch Schwarze Belisario & Nadel LLP

(57) ABSTRACT

An apparatus useful for performing various surgical procedures, including but not limited to plastic surgery such as mid face lifts, neck lifts, brow lifts, under eye lifts, breast lifts, and organ repositioning, includes a body 2, 3, 31, 52 having at least one elongate member 6, 7, 36, 51 and a guide 13, 43, 54 which cooperate to position a suture 60, 65, 120, 130 inside a layer of subcutaneous tissue, from a remote access point. A suture 60, 65 having modified portions 63 is additionally provided for use with the apparatus to implement a desired surgical procedure.

21 Claims, 35 Drawing Sheets

(51) Int. Cl.
*A61B 17/00* (2006.01)
*A61B 90/00* (2016.01)

(52) U.S. Cl.
CPC ............ *A61B 2017/00526* (2013.01); *A61B 2017/00792* (2013.01); *A61B 2017/00796* (2013.01); *A61B 2017/06009* (2013.01); *A61B 2017/06042* (2013.01); *A61B 2017/06052* (2013.01); *A61B 2017/06176* (2013.01); *A61B 2090/0807* (2016.02); *A61B 2090/08021* (2016.02)

(58) Field of Classification Search
CPC ..... A61B 17/28; A61B 17/30; A61B 17/0485; A61B 17/29; A61B 17/04; A61B 2017/2096; A61B 2017/2926; A61B 2017/2927; A61B 2017/2929; A61B 2017/301; A61B 2017/303; A61B 18/1442; A44C 7/001; A44C 7/00
USPC ........ 606/148, 139, 144, 205–210, 113, 147, 606/150, 87
See application file for complete search history.

(56) References Cited

U.S. PATENT DOCUMENTS

| | | | |
|---|---|---|---|
| 1,874,668 A | | 8/1932 | Wadewitz |
| 2,665,692 A | * | 1/1954 | L'Esperance ................. 606/148 |
| 2,860,902 A | | 11/1958 | Diels |
| 2,913,270 A | | 11/1959 | Sachsenroeder, Sr. |
| 3,550,166 A | | 12/1970 | Kotler |
| 3,739,784 A | | 6/1973 | Itoh |
| 3,903,892 A | | 9/1975 | Komiya |
| 3,910,279 A | | 10/1975 | Okada et al. |
| 3,915,419 A | | 10/1975 | Brown et al. |
| 4,008,912 A | | 2/1977 | Kotov |
| 4,306,561 A | * | 12/1981 | de Medinaceli ................ 606/22 |
| 4,312,337 A | * | 1/1982 | Donohue ........................ 606/80 |
| 4,635,636 A | * | 1/1987 | Goldstein ..................... 606/150 |
| 4,638,802 A | | 1/1987 | Okada |
| 4,655,223 A | * | 4/1987 | Kim ............................. 606/148 |
| 5,224,488 A | | 7/1993 | Neuffer |
| 5,318,578 A | | 6/1994 | Hasson |
| 5,480,406 A | | 1/1996 | Nolan et al. |
| 5,569,271 A | * | 10/1996 | Hoel ............................. 606/148 |
| 5,624,446 A | | 4/1997 | Harryman, II |
| 5,645,548 A | * | 7/1997 | Augsburger ..................... 606/87 |
| 5,681,331 A | | 10/1997 | de la Torre et al. |
| 5,707,379 A | * | 1/1998 | Fleenor et al. ................. 606/145 |
| 5,759,188 A | * | 6/1998 | Yoon ............................. 606/147 |
| 5,766,217 A | | 6/1998 | Christy |
| 5,776,150 A | * | 7/1998 | Nolan et al. .................... 606/148 |
| 5,782,845 A | | 7/1998 | Shewchuk |
| D397,218 S | * | 8/1998 | Cadaver ....................... D24/133 |
| 5,807,276 A | | 9/1998 | Russin |
| 5,810,861 A | | 9/1998 | Gaber |
| 6,030,391 A | * | 2/2000 | Brainard et al. ................. 606/87 |
| 6,035,967 A | | 3/2000 | Maeda |
| 6,036,700 A | * | 3/2000 | Stefanchik et al. .......... 606/144 |
| 6,200,327 B1 | * | 3/2001 | Assal ............................. 606/148 |
| 6,347,816 B1 | | 2/2002 | Donaho |
| 6,638,286 B1 | | 10/2003 | Burbank et al. |
| 6,746,471 B2 | * | 6/2004 | Mortier et al. ................ 606/207 |
| 6,749,615 B2 | | 6/2004 | Burdulis et al. |
| 6,770,084 B1 | | 8/2004 | Bain et al. |
| 6,835,193 B2 | | 12/2004 | Epstein et al. |
| 6,936,024 B1 | | 8/2005 | Houser |
| 7,101,378 B2 | | 9/2006 | Salameh et al. |
| 7,198,626 B2 | | 4/2007 | Lee et al. |
| 7,264,623 B2 | * | 9/2007 | Harris et al. .................. 606/148 |
| 7,322,939 B2 | | 1/2008 | Burbank et al. |
| 7,615,062 B2 | * | 11/2009 | Deland ......................... 606/148 |
| 7,771,441 B2 | | 8/2010 | Cerundolo |
| 7,918,868 B2 | | 4/2011 | Marshall et al. |
| 7,955,341 B2 | | 6/2011 | Cerundolo |
| 8,353,920 B2 | * | 1/2013 | Mikkaichi ..................... 606/145 |
| 2001/0025171 A1 | | 9/2001 | Mortier et al. |
| 2004/0102809 A1 | * | 5/2004 | Anderson ..................... 606/232 |
| 2004/0133216 A1 | | 7/2004 | Wulc et al. |
| 2004/0267270 A1 | * | 12/2004 | Jacobs et al. ................... 606/86 |
| 2005/0261581 A1 | | 11/2005 | Hughes et al. |
| 2006/0004409 A1 | | 1/2006 | Nobis et al. |
| 2006/0004410 A1 | | 1/2006 | Nobis et al. |
| 2006/0025819 A1 | | 2/2006 | Nobis et al. |
| 2006/0069398 A1 | | 3/2006 | Suzuki et al. |
| 2006/0217762 A1 | | 9/2006 | Maahs et al. |
| 2006/0282100 A1 | * | 12/2006 | Pasricha et al. .............. 606/148 |
| 2007/0118174 A1 | * | 5/2007 | Chu ............................. 606/207 |
| 2007/0179509 A1 | | 8/2007 | Nagata et al. |
| 2007/0293876 A1 | | 12/2007 | Abe et al. |
| 2008/0082113 A1 | | 4/2008 | Bishop et al. |
| 2008/0172085 A1 | * | 7/2008 | Chiu et al. .................... 606/205 |
| 2008/0294185 A1 | * | 11/2008 | Blomdahl .............. A44C 7/001 606/188 |
| 2009/0062817 A1 | | 3/2009 | Suzuki et al. |
| 2009/0082797 A1 | | 3/2009 | Fung et al. |
| 2009/0082805 A1 | | 3/2009 | Kaiser et al. |
| 2009/0216251 A1 | | 8/2009 | Levine et al. |
| 2009/0216268 A1 | | 8/2009 | Panter |
| 2010/0137679 A1 | | 6/2010 | Lashinski et al. |
| 2010/0331612 A1 | | 12/2010 | Lashinski et al. |
| 2012/0143225 A1 | | 6/2012 | Chin et al. |
| 2014/0275750 A1 | | 9/2014 | Levine |

FOREIGN PATENT DOCUMENTS

| | | |
|---|---|---|
| JP | S63-40559 A | 2/1988 |
| JP | H06-74146 U | 10/1994 |
| JP | H10-216161 A | 8/1998 |
| JP | 2001-198131 A | 7/2001 |
| JP | 2002-028164 A | 1/2002 |
| JP | 04513702 | 5/2004 |
| JP | 2004-526483 A | 9/2004 |
| JP | 3628597 B2 | 3/2005 |
| JP | 2007151615 | 6/2007 |
| JP | 2007-167500 A | 7/2007 |
| JP | 2007-296319 A | 11/2007 |
| WO | 9406357 A1 | 3/1994 |
| WO | 9531149 A1 | 11/1995 |
| WO | 9602197 A1 | 2/1996 |
| WO | WO 98/35616 | 8/1998 |
| WO | 0239905 | 5/2002 |
| WO | 03077771 A1 | 9/2003 |
| WO | 2005096956 A1 | 10/2005 |
| WO | 2006047563 A2 | 5/2006 |
| WO | WO 2007/073931 | 7/2007 |
| WO | 2008042992 A2 | 4/2008 |
| WO | 2008070691 A2 | 6/2008 |
| WO | WO 2009045248 | 4/2009 |

OTHER PUBLICATIONS

Office Action issued Jul. 31, 2014 in AU Application No. 2013204680.
Office Action issued Aug. 15, 2014 in AU Application No. 2013204057.
Office Action issued Sep. 9, 2014 in U.S. Appl. No. 12/384,326 by Levine.
Int'l Search Report and Written Opinion issued Aug. 28, 2014 in Int'l Application No. PCT/US2014/030533.
Office Action issued Jan. 14, 2014 in JP Application No. 2012-503414.
Partial translation of an Office Action issued Mar. 11, 2014 in MX Application No. MX/a/2010/001019.
Office Action issued Jul. 10, 2014 in CA Application No. 2,694,650.
Office Action issued Oct. 1, 2014 in IL Application No. 215256.
English translation of an Office Action issued Oct. 14, 2014 in MX Application No. MX/a/2010/001019.
Office Action issued Oct. 29, 2014 in KR Application No. 10-2010-7003741.

(56) References Cited

OTHER PUBLICATIONS

Office Action issued Jan. 27, 2015 in JP Application No. 2014-002445.
Int'l Preliminary Report on Patentability issued Feb. 6, 2015 in Int'l Application No. PCT/US2014/030533.
Search Report issued Mar. 27, 2015 in EP Application No. 08836569.7.
Office Action issued May 4, 2015 in IL Application No. 226164.
Office Action issued May 21, 2015 in CA Application No. 2,694,650.
English translation of an Office Action issued in MX Application No. MX/a/2010/001019.
Office Action issued Jun. 3, 2015 in U.S. Appl. No. 12/384,326 by Levine.
Office Action issued Sep. 29, 2015 in JP Application No. 2014-002445.
Baumgarten and Wright, "Sliding Knots—Overhand Throw and Duncan Loop", Arthroscopic Knot Tying—An Instruction Manual, Lippincott, Williams & Wilkins, Philadelphia (2005), pp. 32 and 33.
"Knot Tying Illustrations—Easy Slider" and "Knot Tying Illustrations—The Fancy Slider"—Web Publication reviewed Oct. 13, 2010 and "www.utube.com/watch?v=ZJzf1Le00ck" and "www.phoenixsterling.com/IMAGES/Knot%20Tying%20Illustrations.pdf".
McMillan and Caspari, "Arthroscopic Knot-Tying Techniques", An Atlas of Shoulder Arthroscopy, Imhoff, Ticker and Fu, Editors, Martin Dunitz, London (2003), pp. 87 to 95.
Int'l Search Report and Written Opinion issued Oct. 30, 2014 in Int'l Application No. PCT/US2014/024816.
Int'l Preliminary Report on Patentability issued Sep. 24, 2015 in Int'l Application No. PCT/US2014/024816.
Office Action issued Mar. 8, 2016 in MX Application No. MX/a/2010/001019 (translation only).

\* cited by examiner

SURGICAL SUTURING DEVICE AND TOOLS USED THEREWITH

RELATED CASE

This application claims the benefit and priority of U.S. Provisional Application No. 60/962,031, filed on Jul. 26, 2007.

BACKGROUND OF THE INVENTION

The present invention relates to an apparatus capable of enabling a practitioner to thread a suture in a layer of subcutaneous tissue from a remote access point, to surgical methods facilitated by such an apparatus, and to associated tools useful with the apparatus for performing such surgical methods.

Various surgical methods, primarily in the field of plastic surgery, require the placement of a suture deep inside a layer of subcutaneous tissue from a remote access point. The typical procedure used is to first separate the layers of tissue (e.g., the facial tissue) for appropriate access, and to later suture the layers of tissue together, under tension. This, however, requires extensive surgery, which is expensive and which takes a significant amount of time (e.g., a matter of weeks) to heal.

Various procedures have been attempted to reduce the resulting trauma to a patient, the corresponding expense of the procedure, and the time required for recovery.

For example, one attempted procedure has been to implant a device having barbed profiles capable of engaging subcutaneous tissue at a location remote from the point of access. In practice, however, such barbs have been found to be prone to release after a relatively short period of time (on the order of a few months). Release of the barbs then allows the engaged tissue to sag.

Other attempted procedures have made use of suturing devices for facilitating placement of the suture from a remote access point. Such devices, however, are bulky mechanisms which, in practice, require considerable separation of the layers of tissue in order to reach the intended location, and are typically prone to the severing of blood vessels and nerves. Moreover, surgical procedures using such devices are complicated, and typically require the use of an endoscope, adding to the complexity of the desired procedure. Furthermore, such surgical procedures are highly invasive, time consuming and expensive, and require long recovery times.

As a consequence, there has long been a need in surgery, and in particular, facial plastic surgery, for a device which can be used to remotely place a suture and which can enter facial tissue with an incision of minimum-size, so that scarring would not then ensue which could mar the resulting appearance. Further required is a surgical procedure that can provide a long term result by minimizing sagging due to migration of the sutures through tissue due to applied stresses, a problem which is commonly referred to in the art as a "cheese wire effect".

Various suturing instruments are well known in surgical practice, particularly those used in laparoscopic procedures in which the task is to sew together separated tissue, such as incisions made in skin or organs, by remote manipulation. For example, one such instrument is disclosed in U.S. Pat. No. 5,782,845, and includes a first elongated hollow body that can be passed fully through the tissue on one side of a wound or incision, and a second elongated body having an aperture which is passed fully through the other side of the wound or incision. The two bodies are brought together by an alignment device to achieve closure of the wound and to insure that the ends of both bodies meet and coincide, employing what is essentially a lateral motion, for the passage of a suture.

However, because the internal side of the tissue typically contains a free medium such as air or a fluid, a suture threaded through the first body can pass through the aperture of the second body and can issue unimpeded into the internal side. Following this, the suture can be extracted by the second elongated body, having the aperture, and can be withdrawn to the exterior of the tissue, where it can be tensioned and knotted with the end of an opposing suture. Instruments of this type provide no spacings, within or between successive suture stitches.

Other suturing instruments are constructed much like hemostats, which employ a pincing motion that operates from a remote pivot, and are similarly suited for joining and attaching remote tissue.

A further consideration is that in practicing certain surgical procedures, particularly including facial plastic surgery, external manipulation is required from a remote access point, unlike wound closure, which requires local manipulation. The elongated hollow body of an instrument of the type disclosed in U.S. Pat. No. 5,782,845, must be guided by the apparatus for alignment with and for passing through a subcutaneous target aperture, and the guiding and docking motion to be employed must be virtually coincident with the axis of the hollow body. Otherwise, bunching of the tissue will occur, causing an unwanted cosmetic effect. For the example of a desired facial cosmetic surgical procedure, an appropriate alignment device must reference as close to the target aperture as is possible to prevent even slight looseness in the alignment mechanism from magnifying and causing misalignment between the hollow body and the aperture, thereby preventing penetration.

For cosmetic reasons, there is also a need to minimize the size of any apertures. Consequently, for facial cosmetic surgery, it is further necessary to use small diameter hollow bodies (preferably, 1 mm or smaller) to prevent the scarring of skin tissue. Moreover, to further prevent trauma, the surgical apparatus must be capable of storing the suture ends, for later extraction at a common external location on the face where the exposed ends are to be tensioned and tied together to complete the desired procedure.

A further consideration is that because suture material can buckle when subjected to axial compression, the hollow body must be capable of penetrating the aperture and the tissue by a sufficient distance to make room in the subcutaneous tissue for receiving the suture. Otherwise, the suture material will bunch up, and will fail to deploy to an adequate length for capture and extraction at the aperture. The apparatus could additionally be provided with an aperture which collapses with adequate force to clamp the suture ends during extraction.

Because the known devices are not capable of performing in this manner, it has remained desirable to provide a surgical suturing apparatus which can overcome the fundamental deficiencies previously described, to carry out a desired surgical procedure.

SUMMARY OF THE INVENTION

In accordance with the present invention, the foregoing problems are overcome by providing an apparatus which can place a suture deep inside a layer of subcutaneous tissue, from a remote access point, and which can be used to implement a surgical method for performing desired surgical procedures. The apparatus and the corresponding surgical techniques are primarily intended for use in performing plastic surgery, and are particularly described in the context of performing a mid face lift. However, variations of the apparatus and method of the present invention are equally possible for use in performing neck lifts, brow lifts, under eye lifts, breast lifts, organ repositioning, and various other surgical procedures which similarly require the repositioning and the anchoring of tissues.

In its preferred embodiment, the apparatus is a fixture incorporating eyelets or equivalent openings located at a distal end of the fixture and which can enter the scalp or facial skin through tiny punctures or incisions, combined with a guide which is supported by the structure and which establishes a passageway which is aligned with the eyelets (or openings). The guide operates to receive a cannula, or an equivalent device for passing a suture, which penetrates the skin and subcutaneous tissue, passes through the eyelets associated with the fixture, and then exits the skin, coming to rest within an optional external guard. A suture can then be threaded through the cannula so that, following removal of the cannula, the suture passes through the skin and the subcutaneous tissue. Following this, the eyelets are retracted, causing the suture to form a subcutaneous sling having ends which exit at the entry locations for the eyelets, and which can be anchored.

To this end, a preferred procedure is described in which the suture is anchored to the periosteum or to the ligament of the zygomatic arch, with appropriate tensioning for repositioning the engaged tissue in order to achieve the desired cosmetic effect. A fixture is used to sequentially guide the suture along each of the long sides of a rectangle or, as an alternative, a triangle, to penetrate apertures which are subcutaneously located and spaced apart along a common base line, so the ends of the suture are successively set and maintained in a preset spacing.

As a further alternative, a suture is provided having one or more thickened sections that distribute stress in subcutaneous tissue due to tension forces. Such a suture will have applicability to a variety of surgical situations including, for example, situations where tissue or an organ is to be repositioned using a sling formed with the suture, and situations where there is concern that the suture may cut through tissue (i.e., so-called "cheese wire effect").

Various alternative embodiment fixtures and cannula structures are provided. One such fixture includes a pair of bodies connected by a hinge. One body includes a pair of elongate members having eyelets formed in distal ends of the elongate members, and the other body includes a guide for receiving a cannula so that the cannula can be passed through the eyelets of the elongate members, for properly locating a suture which is passed through the cannula. Another fixture includes a mechanism for adjusting the spacing between the pair of elongate members which incorporate the distal eyelets. Another fixture includes a single elongate member with a single eyelet. Another fixture includes a single elongate member which houses a pair of arms that can be extended to the desired subcutaneous location. Each of the arms incorporates an eyelet through which a suture can be passed.

Each of the alternative embodiment fixtures includes a guide for receiving a cannula for passing a suture. The cannula can be formed as a solid structure, or as a hollow tubular structure having one or more openings for passing a suture received by the cannula, for selective deployment in adjacent tissue. As an alternative, a suture including an attached needle for leading the suture can be used instead of the cannula.

In a method which is presently considered to be preferred for mid face lifts, a sling formed by the suture is anchored to the zygomatic periosteum or ligament. This is preferably done using miniature tools which allow the size of the facial incisions to be kept to a minimum. The suture is externally manipulated to create the sling by threading the suture deep within a layer of tissue in a rectangular or acute triangular pattern.

A further discussion of preferred apparatus for performing described surgical procedures is provided below, taken together with the following drawings.

DETAILED DESCRIPTION OF PREFERRED EMBODIMENTS

Figure 1:
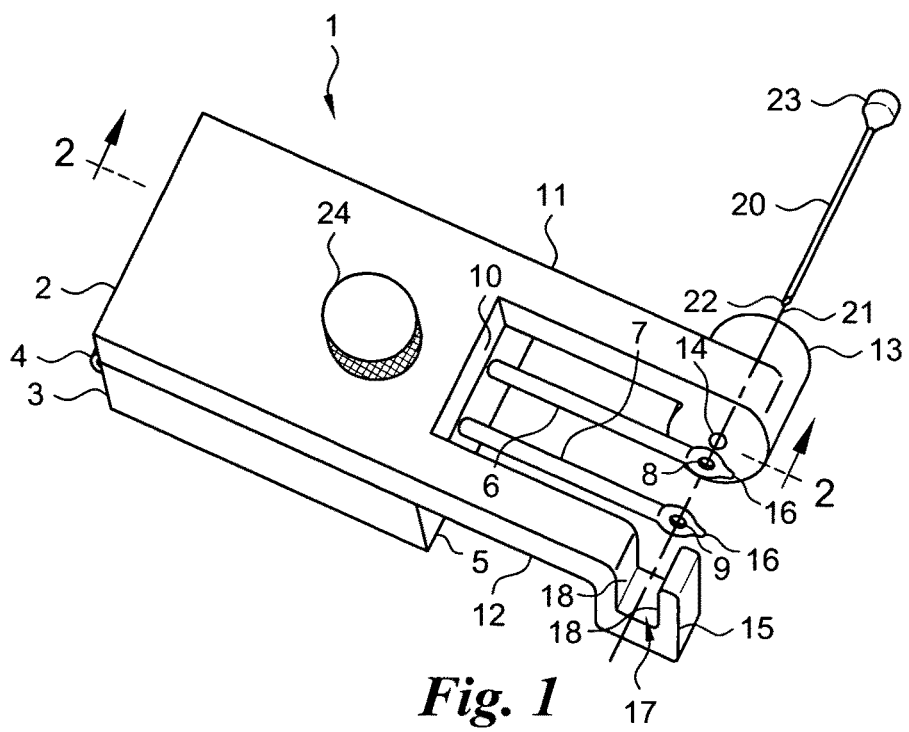
FIG. 1 is an isometric view of a first, alternative embodiment of the fixture and cannula of the present invention.

FIG. 1 shows a first, alternative embodiment of the apparatus of the present invention, which is presently considered as being preferred. The fixture 1 generally includes an upper body 2 and a lower body 3 connected by a live hinge 4. As alternatives, other hinge configurations can also be used including, as an example, a dowel, etc., or the bodies 2, 3 can be assembled without a hinge, if desired. The bodies 2, 3, as well as other components of the various embodiments of the fixture to be described, can be formed of any of a variety of materials that offer a sterile field, including various plastics and metals.

The lower body 3 includes an end face 5 opposite to the hinge 4, and a pair of elongate members 6, 7 extend from the end face 5. The elongate members 6, 7 can be solid or hollow, and are preferably 2 to 3 mm in width or diameter although other thicknesses are acceptable. The distal ends of the elongate members 6, 7 each include an eyelet 8, 9, respectively, and can further include pointed tips 16, if desired, to facilitate entrance of the elongate members 6, 7 into small incisions. The eyelets 8, 9 preferably have the shape of an elongated hole, but can be oval or circular, if desired. Alternately, the eyelets 8, 9 can be replaced with hooks extending from the tips of the elongate members 6, 7, or can take the form of probes (or webs) extending from the tips of the elongate members 6, 7 which can be formed of a pierceable material.

Typically, the elongate members 6, 7 will have a length on the order of 3 to 4 cm, although various other lengths can be employed. As an alternative, the lengths of the elongate members 6, 7 can be made adjustable, to allow the fixture to penetrate inside subcutaneous tissue for various distances. The elongate members 6, 7 are typically spaced apart by approximately 1 cm, although other spacings can also be used, and the selected spacing can also be made adjustable, as will be described more fully below.

The upper body 2 also includes an end face 10 opposite to the hinge 4, adjacent to the end face 5 of the lower body 3. A pair of arms 11, 12 extend from the end face 10, preferably from opposing side faces of the upper body 2, in general alignment with the elongate members 6, 7 extending from the end face 5 of the lower body 3.

Figure 2:
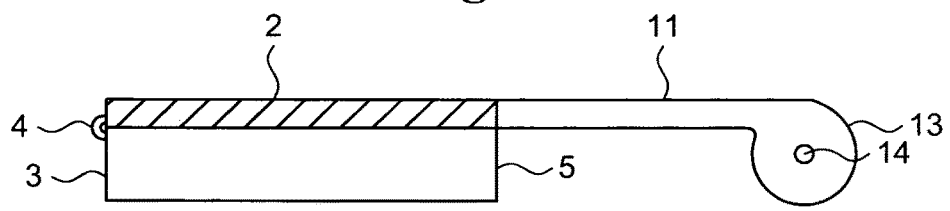
FIG. 2 is a cross-section of the fixture shown in FIG. 1, taken along the line 2-2.

As is further shown in FIG. 2, the distal end of the arm 11 is provided with a guide 13 which is oriented substantially perpendicular to the longitudinal axis of the arm 11, and which is spaced from the elongate members 6, 7. The guide 13 includes a keying structure such as the aperture 14 for receiving a cooperating suture-feeding structure, as will be described more fully below. The aperture 14 is preferably concentric with the guide 13 so the suture-feeding structure will be oriented substantially perpendicular to the longitudinal axis of the arm 11.

Figure 3:
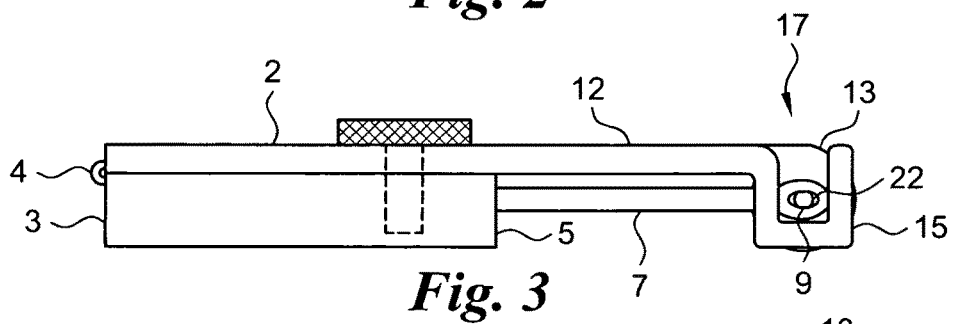
FIG. 3 is a side elevation of the fixture shown in FIG. 1, in a closed position.

As is further shown in FIG. 3, the distal end of the arm 12 is provided with a guard 15 which is once again oriented substantially perpendicular to the longitudinal axis of the arm 12. The guard 15 defines an open region 17 for receiving the end of the suture-feeding structure, as will be described more fully below, primarily for purposes of receiving the end of the suture-feeding structure in a manner that helps prevent prick injury of the user of the fixture. The guard 15 also serves to depress tissue, to facilitate the exit of a cannula from subcutaneous tissue, as will be described more fully below. As an alternative to the guard 15, a spatula or some other equivalent structure can also be used to depress the tissue.

The guide 13 and the aperture 14 operate to direct a suitable suture-feeding structure, such as the illustrated cannula 20, along a centerline 21 which extends through the guide 13, the eyelets 8, 9 of the elongate members 6, 7, and into the guard 15. Such structures operate to control the traverse of the cannula 20 through the subcutaneous tissue following desired penetration of the skin, to be more fully described below, enabling the cannula 20 to penetrate the eyelets 8, 9 following penetration of the skin, and to exit the skin within the protective, open region 17 of the guard 15.

The guide 13, the eyelets 8, 9 and the guard 15 are preferably concentrically aligned with the centerline 21, with opposing faces 18 of the guard 15 being located within a few millimeters of the centerline 21. One end 22 of the cannula 20 includes a sharpened tip capable of penetrating tissue. The other end 23 of the cannula 20 is configured to receive a suture, as will be described more fully below, and is preferably implemented as a conventional hub. The use of a hub is preferred to provide a smooth tapered entrance along the inside diameter of the cannula 20, to allow the suture to be smoothly threaded into the cannula 20. As alternatives, the end of the cannula 20 can be located at the end of the hub, for easy entrance by the suture, the end of the cannula 20 can be provided with a thickened section proximal to the tip 22, or a hubless cannula 20 can be used.

The exposed length of the cannula 20, from the hub to the tip, is set so that the sharp tip 22 does not protrude beyond the guard 15 when the cannula 20 is inserted into the aperture 14 of the guide 13 and through the eyelets 8, 9, and the hub is thrust to a forward-most position against the point of entrance to the guide 13, to provide the cannula 20 with a length appropriate for insuring that the sharp tip 22 rests within the guard 15. The dimensions of the aperture 14 and the eyelets 8, 9 are preferably selected to accommodate a sharpened, 21 gage cannula. However, various other dimensions can be employed to accommodate different cannula sizes.

To be noted is that the fixture 1 shown in FIGS. 1 to 4 is designed for use on the left side of the face of a patient. As an alternative, and to function on the right side of the face of a patient, the arms 11 and 12 can be switched, reversing the locations of the various structures illustrated.

Figure 4:
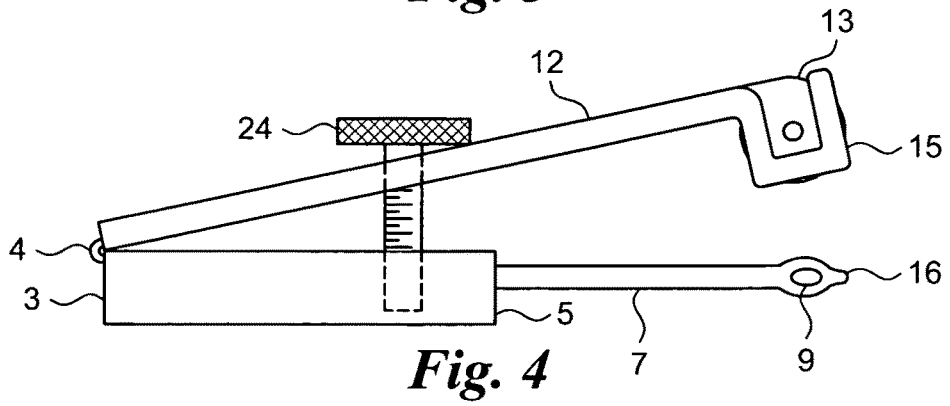
FIG. 4 is a side elevation of the fixture shown in FIG. 1, in an opened position.

FIG. 3 shows the upper body 2 in contact with the lower body 3, for establishing the previously mentioned structural interactions. FIG. 4 shows separation of the upper body 2 from the lower body 3, so that the arms 11, 12, the guide 13 and the guard 15 are rotated upwardly and away from the elongate members 6, 7 of the lower body 3. Such rotation permits free access by the elongate members 6, 7, for insertion into incisions in the tissue being treated. A thumb screw 24 extending between the upper body 2 and the lower body 3 is preferably used to allow the structures to be separated, and to fasten the structures together so the aperture 14 of the guide 13, the eyelets 8, 9 and the guard 15 are concentric, as previously described. Other devices can be used in place of the thumb screw 24, such as a face cam which can rotate on the same axis as the screw so that clamping forces are applied between the upper body 2 and the lower body 3, if preferred.

Figure 5:
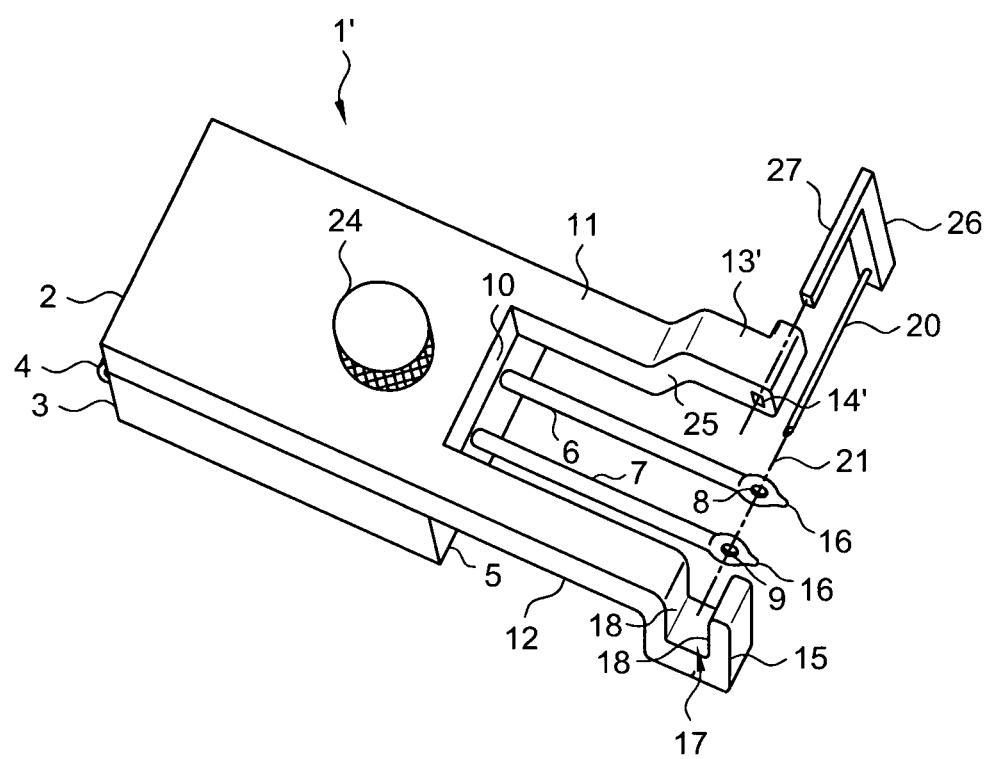
FIG. 5 is an isometric view of an alternative embodiment fixture having an offset guide for establishing a path for the cannula.

FIG. 5 shows an alternative embodiment fixture 1' having various features in common with the fixture 1, but which exhibits some variations. In the description which follows, components corresponding to those previously described have corresponding reference numbers.

The alternative embodiment fixture 1' shown in FIG. 5 replaces the guide 13 of the fixture 1 shown in FIGS. 1 to 4 with an offset guide 13'. Resulting from the offset 25 of the guide 13', the longitudinal axis of the aperture 14' of the guide 13' will be offset relative to the centerline 21 extending though the eyelets 8, 9 associated with the elongate members 6, 7. A jig 26 is coupled with the cannula 20 for engaging the aperture 14', or some other keying structure associated with the guide 13', so that the cannula 20 is brought into alignment with the centerline 21 when the key 27 of the jig 26 is inserted into the aperture 14' of the guide 13'. The key 27 and the aperture 14' are preferably provided with mating, squared cross-sections to facilitate subsequent alignment of the cannula 20 with the eyelets 8, 9 of the elongate members 6, 7.

Figure 6:
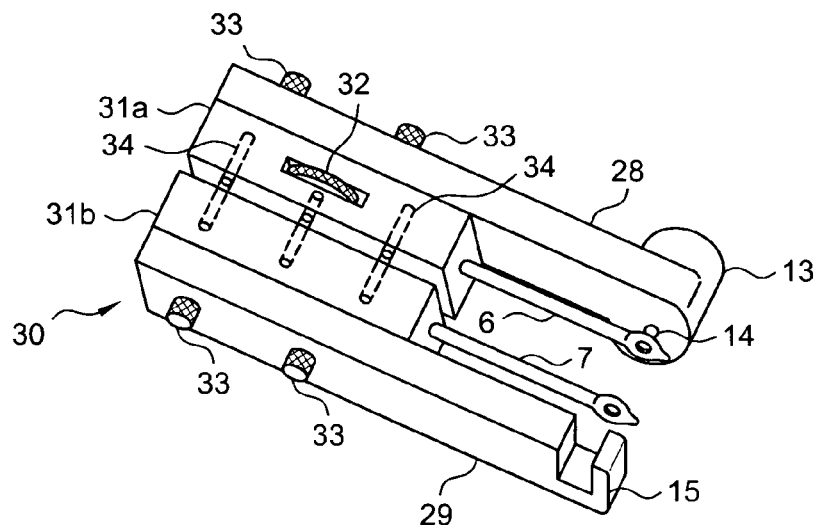
FIG. 6 is an isometric view of an alternative embodiment fixture having an adjustment feature.

FIG. 6 shows an alternative embodiment fixture 30 having various features in common with the fixture 1, but which further exhibits some variations. The fixture 30 employs a single body 31, which replaces the lower body 3 of the fixture 1 and which is split into sections 31a and 31b. A thumb screw 32 adjusts the spacing between the sections 31a and 31b, which controls the distance between the elongate members 6, 7 which extend from the body sections 31a, 31b. Pins 34 are provided to maintain alignment of the body sections 31a, 31b as the thumb screw 32 is adjusted. Rather than being associated with a separate body portion, the arms 28, 29 of the fixture 30 are assembled onto the body sections 31a, 31b using, for example, the knurled screws 33 illustrated.

As an alternative, adjustable bodies similar to the upper body 2 and the lower body 3 of the fixture 1 could similarly be employed by appropriately splitting the upper body 2 and the lower body 3 into sections and by providing the separate sections with an adjustable feature similar to the thumb screw 32.

Figure 7:
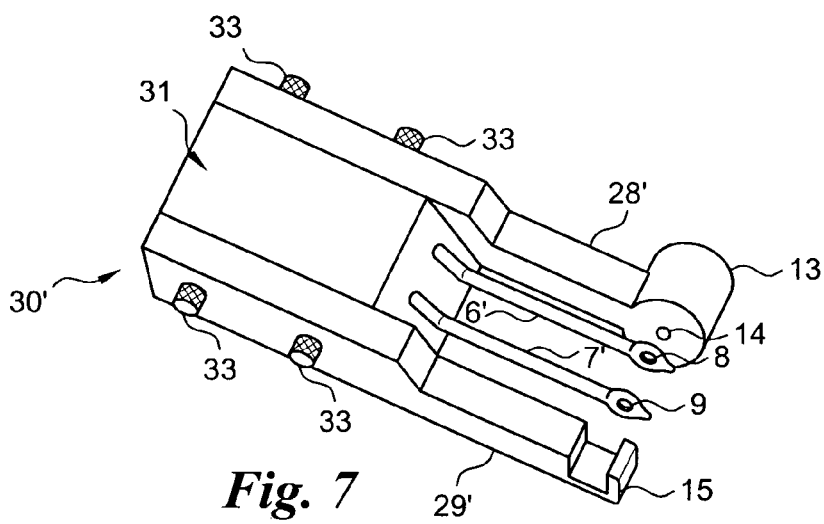
FIG. 7 is an isometric view of an alternative embodiment fixture including elongate members having a curvature.
Figure 8:
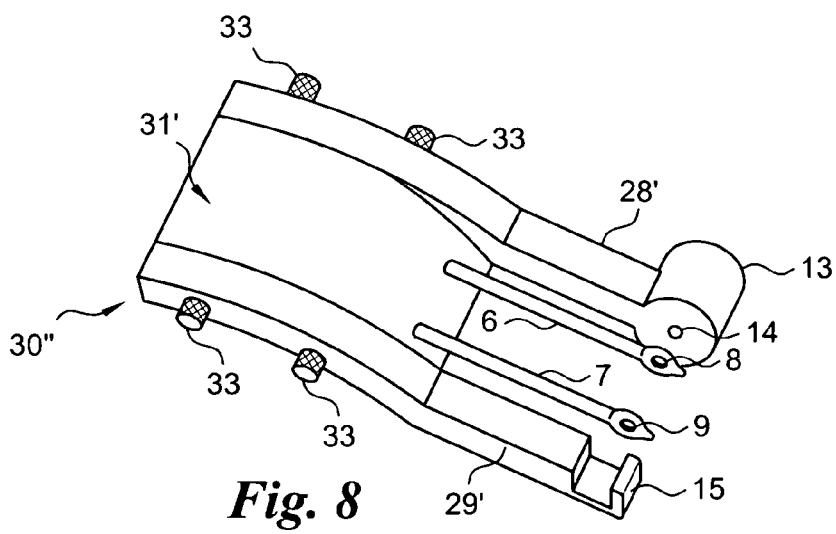
FIG. 8 is an isometric view of an alternative embodiment fixture including a body having a curvature.

FIGS. 7 and 8 show additional alternative embodiment fixtures having features in common with the fixture 30. The alternative embodiment fixture 30' shown in FIG. 7 replaces the straight elongate members 6, 7 of the fixture 1, 30 with elongate members 6', 7' which are bent or contoured, and replaces the straight arms 28, 29 with arms 28', 29' which are bent or contoured. The alternative embodiment fixture 30" shown in FIG. 8 replaces the planar body 31 of the fixture 30 with a body 31' which is bent or contoured.

The planar bodies 2, 3 of the fixture 1 could similarly be replaced with bodies which are bent or contoured, if desired, and combinations of contoured bodies and elongate members can also be employed. Such variations assist in entry into various sections of the face, such as beneath the eye or over the brow, as will be more fully described below. For procedures beneath the eye, bent or contoured elongate members can be used to avoid contact with the eye, and for the case of a brow lift, bent or contoured bodies can be used to follow the shape of the skull over the brow.

As previously, the fixture 30 shown in FIG. 6 and the alternative embodiments shown in FIGS. 7 and 8 are designed for use on the left side of the face of a patient. As a further alternative, and to function on the right side of the face of a patient, the arms and elongate members can be suitably switched, reversing the locations of the various structures illustrated.

Figure 9:
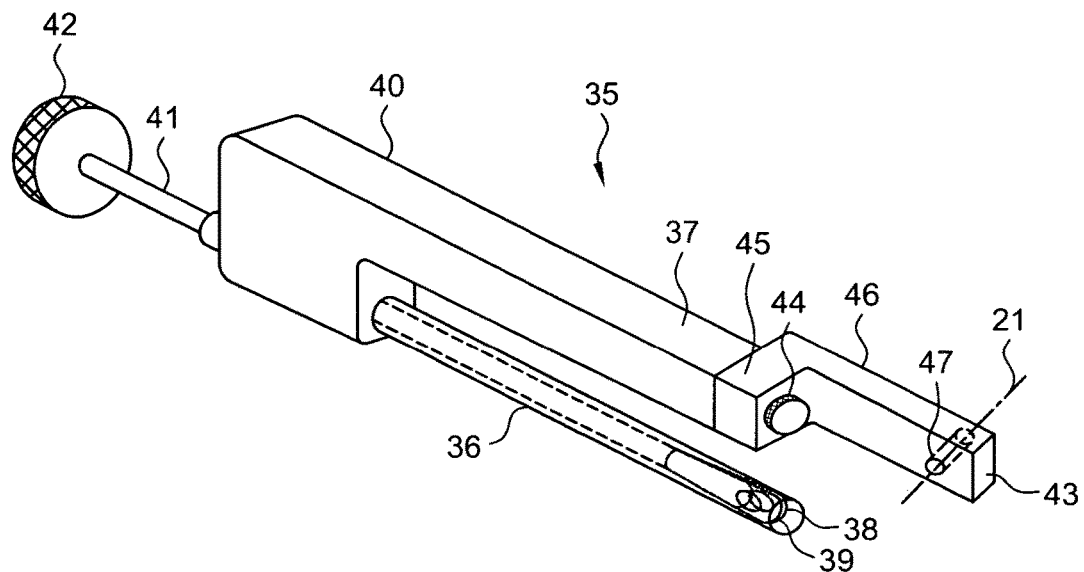
FIG. 9 is an isometric view of an alternative embodiment fixture having a single elongate member containing a pair of extendable arms.
Figure 10:
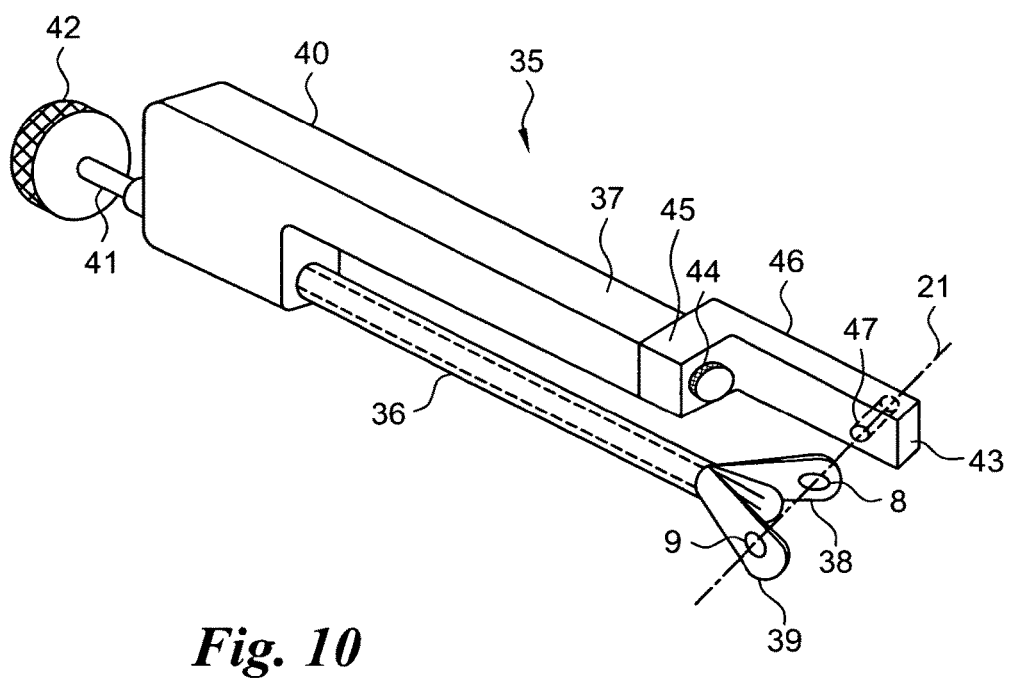
FIG. 10 is an isometric view of the alternative embodiment fixture shown in FIG. 9, with the arms extended from the single elongate member.

FIGS. 9 and 10 show an alternative embodiment fixture 35 having a single elongate member 36 and a single arm 37. The elongate member 36 is formed as a hollow tube which houses a pair of extensions 38, 39. The tube 36 is supported by a handle 40 which incorporates the arm 37. A shaft 41 is slidingly received within the tube 36, and is coupled with the extensions 38, 39. The shaft 41 is further provided with knob 42 for facilitating reciprocation of the shaft 41 as will be more fully described below.

In FIG. 9, the shaft 41 and knob 42 are shown in a retracted position for drawing the extensions 38, 39 fully inside the tube 36. In FIG. 10, the shaft 41 and knob 42 have been plunged forward, causing the extensions 38, 39 to project from the tube 36. The extensions 38, 39 can be spring loaded so the extensions will separate when deployed, in turn causing the eyelets 8, 9 provided at the ends of the extensions 38, 39 to be spaced apart, similar to the spacing developed between the eyelets 8, 9 associated with the elongate members 6, 7 of the fixture 1. Typically, a separation on the order of approximately 1 cm will result from this, although other spacings can also be developed.

A guide 43, similar in function to the guide 13 of the fixture 1, 30, is assembled onto the arm 37 using, for example, a knurled screw 44. The knurled screw 44 is used to secure a flange 45 associated with the guide 43 to the arm 37, and a lug 46 extending from the flange includes an aperture 47 similar to the aperture 14 of the guide 13. When deployed, the aperture 47 of the guide 43 will be concentric with the eyelets 8, 9 of the extensions 38, 39.

Figure 11:
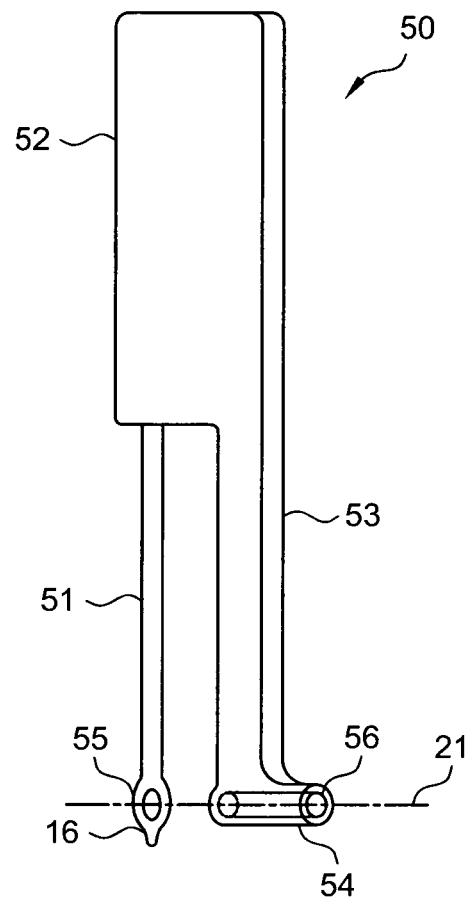
FIG. 11 is an isometric view of an alternative embodiment fixture having a single elongate member.

FIG. 11 shows an alternative embodiment fixture 50 having various features in common with the fixtures 1, 30, but which includes certain simplifications in structure. To this end, the fixture 50 has a single elongate member 51, corresponding in structure to one of the elongate members 6, 7 associated with the fixture 1, which is fixed relative to the handle 52 of the fixture 50. An arm 53 extending from the handle 52 includes a guide 54, similar to the guide 13 associated with the fixture 1, fixed to the arm 53. The guide 54 includes an aperture 56 which is concentric with an eyelet 55 associated with the elongate member 51.

As previously, the fixture 35 shown in FIGS. 9 and 10, and the alternative fixture 50 shown in FIG. 11, are both designed for use on the left side of the face of a patient. As a further alternative, and to function on the right side of the face of a patient, an opposite-hand guide can be provided for reversing the position of the guide relative to the elongate members illustrated.

Examples of various surgical procedures which can be performed using the above-described devices are given in description which follows. Although this description is primarily directed to surgical procedures for performing a mid face lift, and while other lifting procedures will be more briefly described, including neck lifts and forehead lifts, it is to be understood that any of a variety of different surgical procedures can similarly be performed, and that the steps employed in performing such procedures can freely be varied responsive to the requirements and preferences of the surgeon or other practitioner performing a particular procedure.

Various sutures and tools will also be referred to during the description of surgical procedures which is to follow. It is to be understood that such sutures and tools are provided for purposes of facilitating the procedures to be described, but that use of these sutures and tools is optional. Conventional surgical instruments can also be used, if preferred, and the various sutures and tools can either be used in the manner described, or in conjunction with other procedures described herein or developed by the skilled practitioner. For these reasons, and to facilitate the description of the surgical procedures which follows, the various sutures and tools will now be described in general terms, without reference to any particular procedure.

Any of a variety of conventional sutures can be used to perform the surgical procedures being described, including natural, synthetic and metallic suture materials of appropriate diameter and length. As an alternative, sutures having various anchors or other tissue-engaging features can be used to facilitate suture placement.

Figure 12:
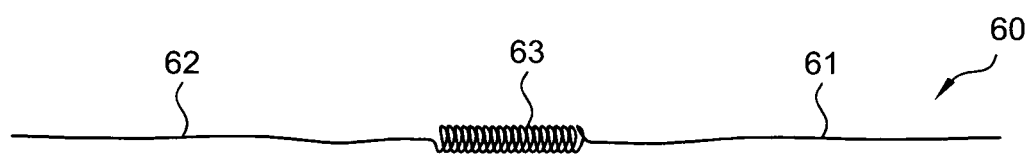
FIG. 12 is a plan view of a first, alternative embodiment suture which can be used with the fixture to perform a surgical procedure.

FIG. 12 shows a tissue-engaging suture 60 which includes sections 61, 62 formed of an otherwise conventional suture material, separated by a modified portion 63. In the configuration shown, the modified portion 63 is implemented as a thickened section which is preferably centrally located between the sections 61, 62. Additional modified portions 63, separating additional sections of otherwise conventional suture material, can also be provided if indicated. It has been found that, in practice, such a suture construction can distribute stress better than a conventional suture. Such a suture construction also enhances retention of the suture in position, and further prevents the well known problem caused when conventional sutures improperly migrate through tissue (i.e., so-called "cheese wire effect").

As an example, the thickened portion can have a length of approximately 1 cm, and a thickness on the order of 1 mm. Various techniques can be used to provide the suture 60 with a thickened section, including knotting, braiding, weaving, molding, the affixing of a sleeve, beading, coiling, kinking, etc. Many of these techniques can be used to develop absorbent regions, and crevices capable of providing beneficial cavities into which tissue growth can penetrate, in turn providing additional bonding.

Figure 13:
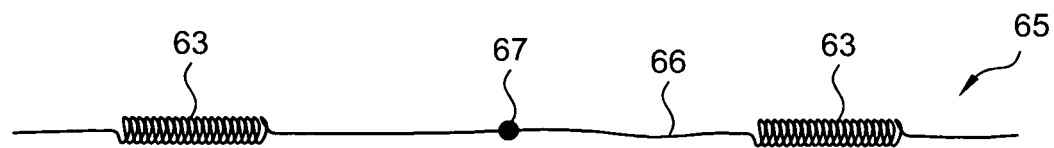
FIG. 13 is a plan view of a second, alternative embodiment suture which can be used with the fixture to perform a surgical procedure.

FIG. 13 shows another tissue-engaging suture 65. The suture 65 includes a pair of modified portions 63 which are separated by a center section 66 formed of an otherwise conventional suture material. To be noted is that when used with the fixture 50 shown in FIG. 11, which is presently considered to be the preferred fixture for use with the suture 65, the thickened sections must have a sufficient diameter to prevent concurrent passage of the suture 65 up the penetrating channel developed by the elongate member 51. The center section 66 is further preferably provided with a marker 67, or with one or more knots positioned at 67, to facilitate alignment of the suture 65 when in use. For use with other embodiments of the fixture (1, 30, 35), the thickened sections 63 should similarly have a sufficient diameter to prevent concurrent passage of the suture 65 up the penetrating channels developed by the various elongate members associated with such apparatus.

Figure 14:
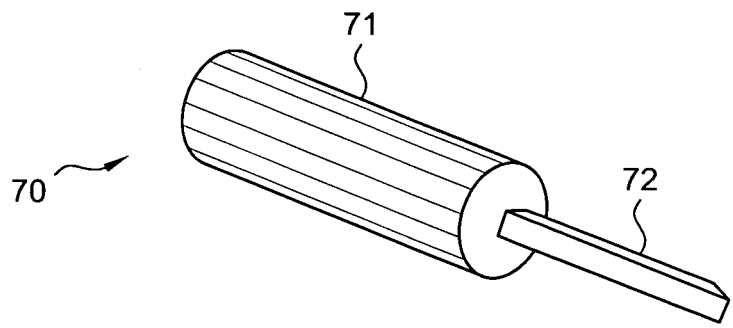
FIG. 14 is an isometric view of a narrow blade scalpel.

FIG. 14 shows a conventional, narrow blade scalpel 70 having a handle 71 and a blade 72. The blade 72 preferably has a width of approximately 1 to 1.5 mm, to produce an incision which is suitable for accommodating the elongate member or members of the fixture being used.

Figure 15:
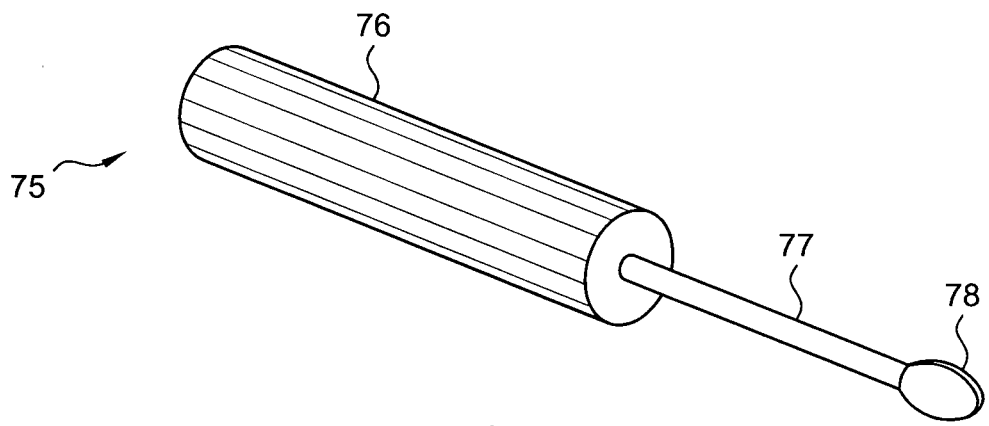
FIGS. 15 and 16 are isometric views of dissecting tools.

FIG. 15 shows a dissecting tool 75 having a handle 76 and a shank 77. The shank 77 preferably has a length of approximately 4 cm. The end of the shank 77 is provided with a dull blade 78, which can either be straight or curved, as shown.

Figure 16:
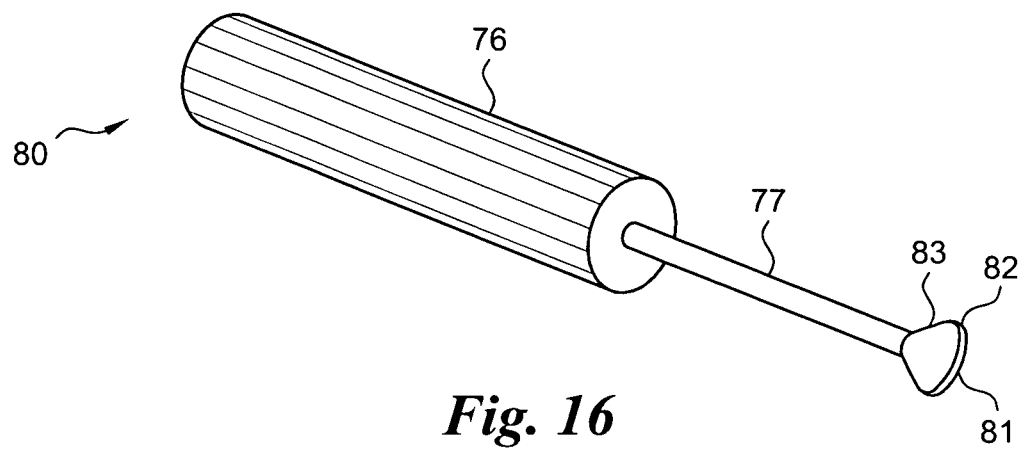

FIG. 16 shows an alternative embodiment for the dissecting tool 75 shown in FIG. 15. The dissecting tool 80 shown in FIG. 16 substantially corresponds to the tool 75, except for the blade 81 of the tool 80, which has a trapezoidal shape. Compared to a typical straight blade, the trapezoidal blade 81 facilitates entry of the tool 80 into small incisions or punctures because the corner angles 82 can first enter the incision, causing the tissue at the incision to be stretched, in turn permitting entry of the opposite side of the blade 81. A reversed procedure can be used during removal of the blade 81 from the incision. The sloping sides 83 of the trapezoidal blade 81 also prevent the tool 80 from snagging on tissue as the blade 81 is retracted.

Figure 17:
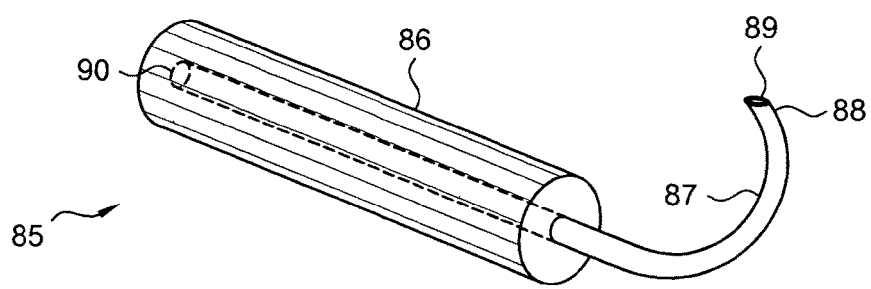
FIGS. 17 and 18 are isometric views of ligament handlers.
Figure 18:
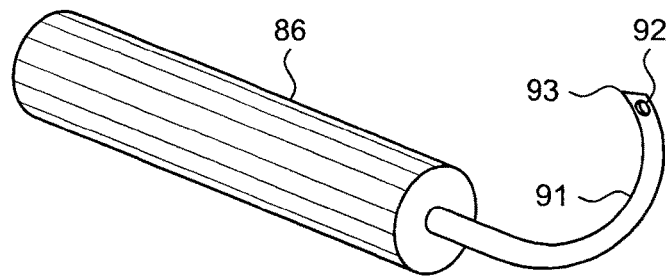

FIG. 17 shows a preferred ligament handler 85 having a handle 86 and a curved cannula 87. The cannula 87 is preferably approximately 18 gage, having a radius of curvature which matches the spacing between the incisions which are to be made, as will be described more fully below, and a sharpened tip 88. An aperture 89 is provided in the tip 88 of the cannula 87, and is preferably tapered to meet the inside diameter of the cannula 87 so that a suture can easily be threaded through the cannula 87. As alternatives, the cannula can extend to the proximal end 90 of the handle 86 so that a suture can easily be threaded through both the cannula 87 and the handle 86, either from the tip 88 or from the proximal end 90 of the handle 86, or the cannula 87 can be replaced with a solid curved needle 91 having an eyelet 92 adjacent to a distal sharpened tip 93, as is shown in FIG. 18.

Figure 19:
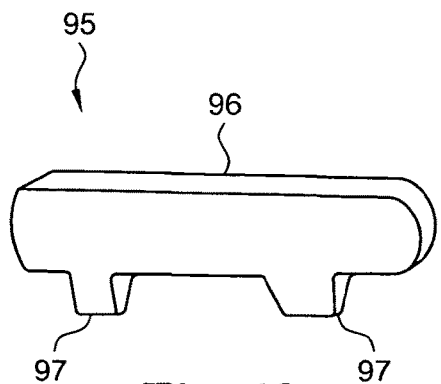
FIG. 19 is an isometric view of a tissue-marking tool.

FIG. 19 shows a tool 95 which can be used to mark the tissue where entry incisions are to be made. The tool 95 includes a handle 96 and a pair of dull marking probes 97. The probes 97 are preferably spaced apart by approximately 1 cm, and operate to depress the tissue enough to temporarily make a mark in the tissue, but not enough to puncture the tissue. The tool 95 eliminates the need for marking pens, which can be messy.

Figure 20:
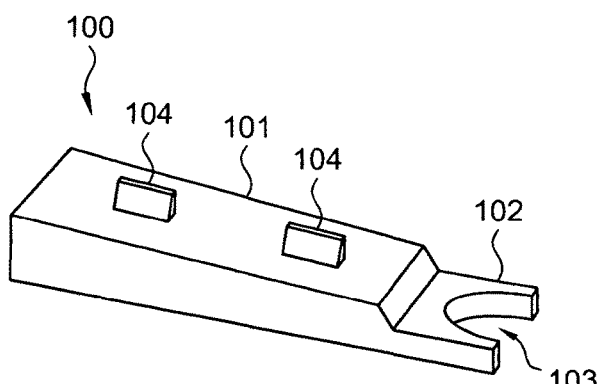
FIG. 20 is an isometric view of a guiding tool which includes a tissue-marking tool.

FIG. 20 shows a tool 100 which can be used to guide the ligature handler to safely penetrate skin and subcutaneous tissue, as will be described more fully below. The guide 100 includes a handle 101 having a forked distal end 102 which defines a region 103 for assisting the ligature handler in safely exiting the skin from subcutaneous tissue. The handle 101 of the tool 100 can additionally be provided with probes 104, similar to the probes 97 of the tool 95, making the tool 100 double purpose and eliminating the need for the separate tool 95 shown in FIG. 19.

Figure 21:
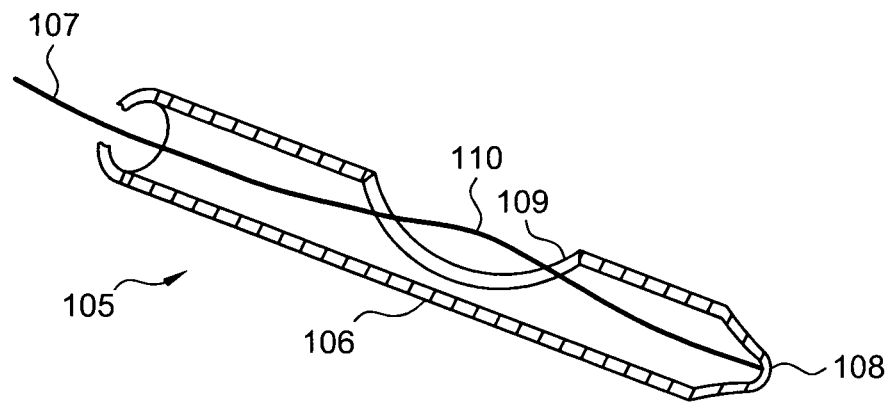
FIGS. 21 and 22 are sectioned, isometric views of a suture engagement tool.
Figure 22:
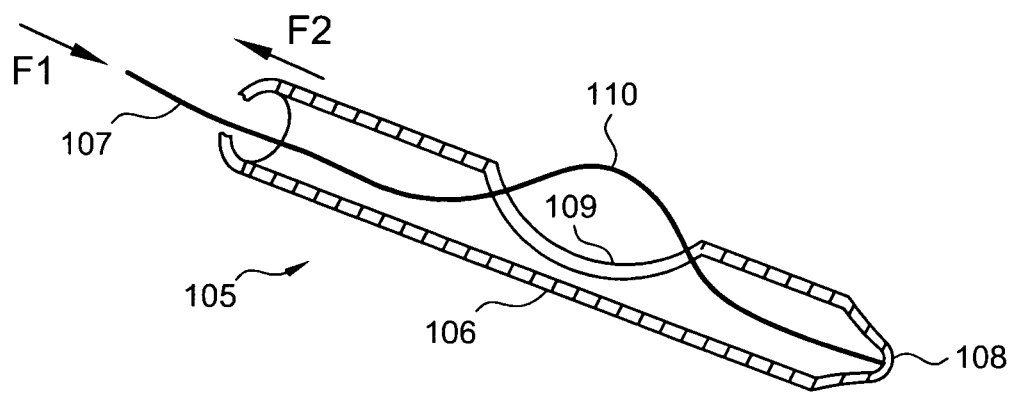

FIGS. 21 and 22 show a tool 105 which is capable of assisting in the subcutaneous handling of a suture. The tool 105 includes a cannula 106 for housing a wire 107. The proximal end of the wire 107 is fixed to the proximal end of the cannula, at 108, and the cannula 106 has an opening, at 109. Referring to FIG. 22, a force F1 applied to the wire 107 is met with a reactive force F2 developed in the cannula 106. As a result, a portion 110 of the wire 107 located at the opening 109 is caused to bend and extend from the opening 109. The portion 110 can have a slight pre-bend, or shape memory, to assist in deformation of the wire 107 in the direction which is preferred for the wire 107 to deploy from the opening 109. The wire 107 can similarly be retracted into the cannula 106 by reversing the forces applied to the wire 107 and the cannula 106, and as a result, straightening the wire 107. Various mechanisms can be attached to the wire 107 to cause the wire to bend and to cause the wire to straighten, if desired. The tool 105 can in this way be used as an expandable eyelet for selectively engaging a suture, including blind sutures.

An example of a surgical procedure will now be described which can be practiced to perform a mid face lift. It is to be understood that while the steps to be described are presently considered preferred, such procedures can be varied responsive to the requirements of a given procedure, and the preferences of the surgeon or other practitioner performing such a procedure, and can similarly be used to perform other surgical procedures either using the steps which will be described below, or suitable variations of such steps, such as variations in the method of entry and anchoring.

The initial steps of the overall procedure are preferably performed to establish an anchor which will later be used to secure the face lift suture (or "sling"). As an alternative, establishment of the anchor can be postponed until after placement of the suture sling, which will be further described below. In either case, the location of the anchor for a mid face lift is preferably in the periosteum or the ligament on the zygomatic arch of the upper face.

Figure 23:
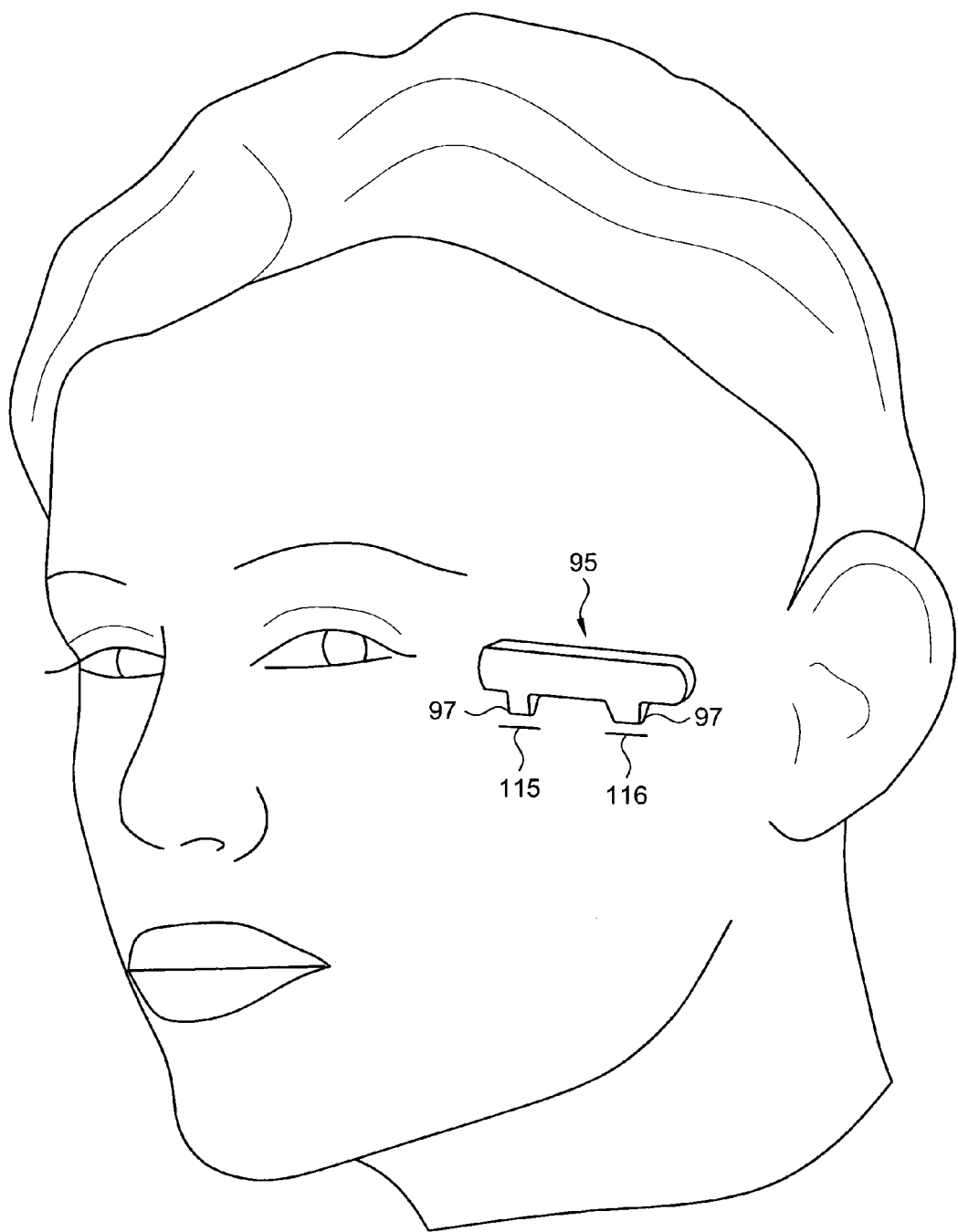
FIGS. 23 through 39 are sequential illustrations providing an example of one of the surgical procedures which can be performed in accordance with the present invention.

Referring to FIG. 23, the tool shown in FIG. 19 is first used to make two temporary depression marks 115, 116 in the skin of the patient. These marks establish the intended locations for the entry incisions to be made, the spacing between the entry incisions, and an angle for the incisions which establishes the vector angle of the lift to be performed. The vector angle is typically perpendicular to a line drawn between the two marks.

Figure 24:
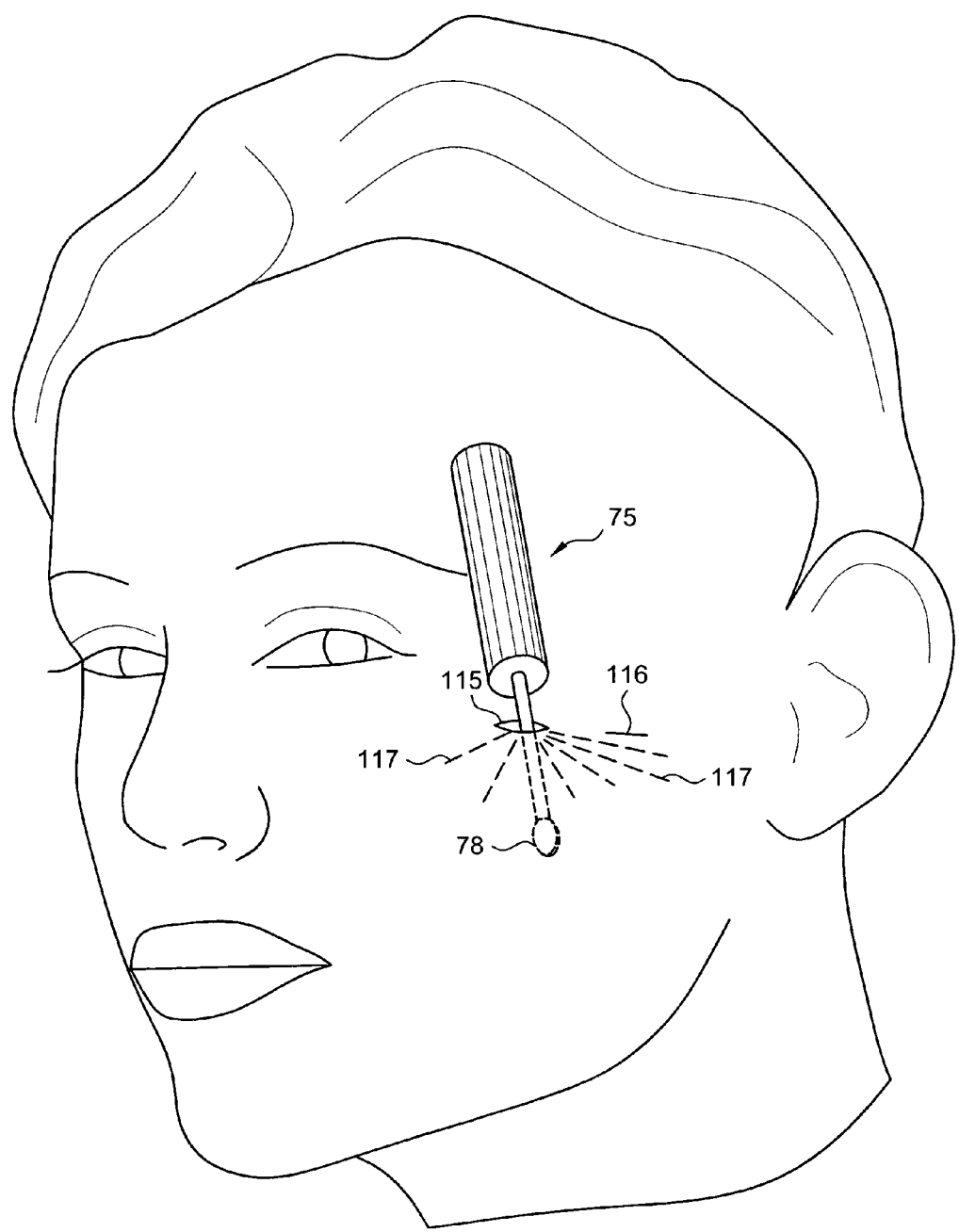

Referring next to FIG. 24, the straight shank scalpel shown in FIG. 14 is used to make a first incision of the skin and subcutaneous tissue, at the location 115. The direction of the puncture is perpendicular to the plane of the skin, typically to the depth of the underlying bone. The location 116 will later be penetrated, in a subsequent step, as will be described more fully below.

FIG. 24 also shows the dissecting tool 75 of FIG. 15 entering the incision 115. The dissecting tool 75, or in the alternative, the dissecting tool 80 of FIG. 16, is used to create pathways which can free up layers of subcutaneous tissue. This is a standard "undermining" technique which is used to separate layers of subcutaneous tissue in the region of the incision, and which can relieve portions of the fat layer, as may be required for cosmetic reasons. Entry of the elongate member 7 of the fixture 1 shown in FIGS. 1 to 4 into the incision 115 establishes the path that the elongate member 7 will follow. Plural dissections, shown by the dotted lines 117, are spread from the incision 115 at various angles and are shorter than the path for the elongate member 7 to avoid undermining in the region where the suture sling is later to be located.

Figure 25:
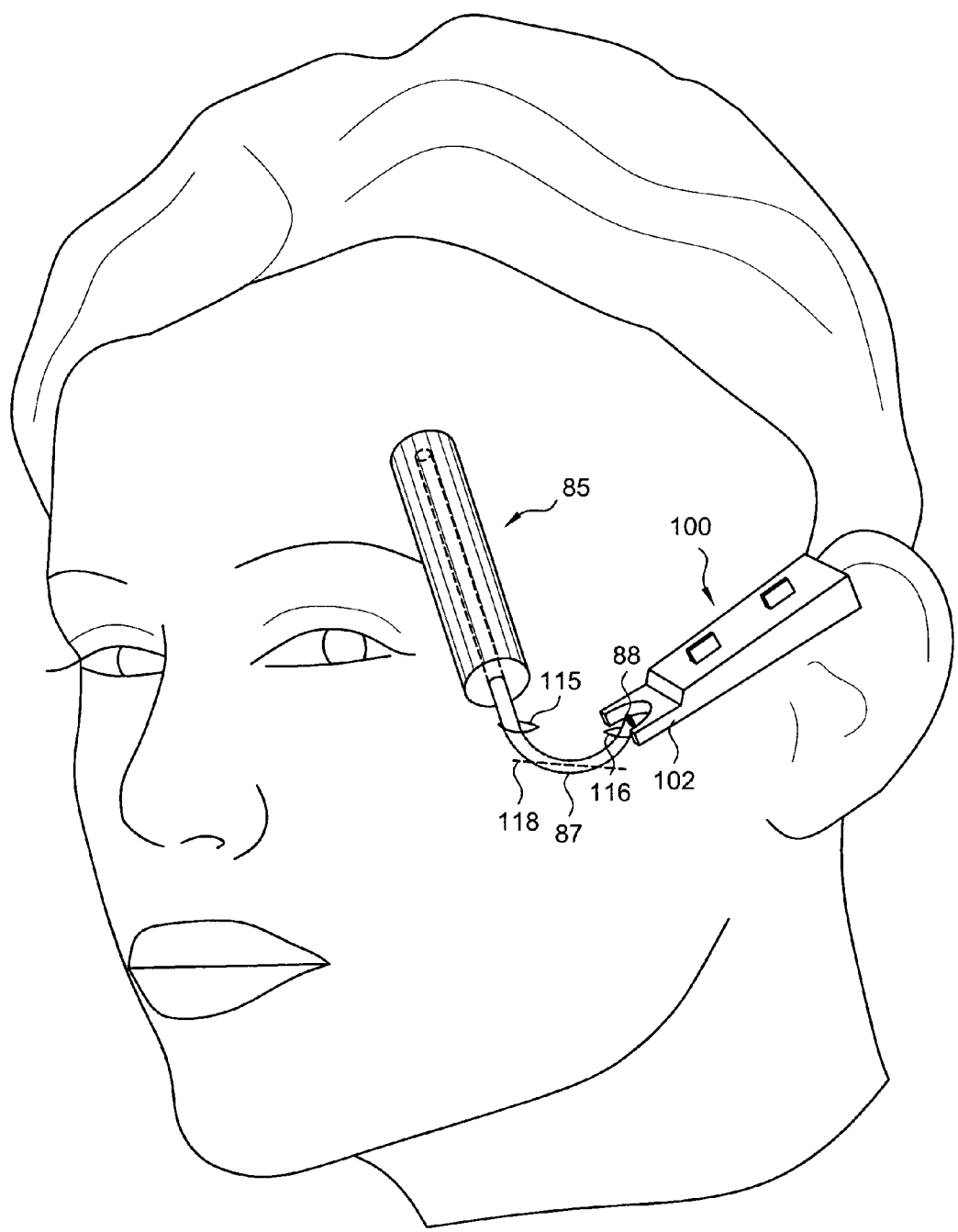

Referring next to FIG. 25, the tip 88 of the cannula 87 of the ligament handler 85 shown in FIG. 17 (or another suitable suture passer) is caused to penetrate the skin, at 115, and is guided by hand to penetrate the subcutaneous tissue and reach the bone of the zygomatic arch (shown at 118). The cannula 87 is further caused to snag the periosteum or the ligament, and the tip 88 is then guided toward the location 116. The tool 100 shown in FIG. 20 is then used to facilitate exit of the tip 88 of the cannula 87 from the skin.

To this end, the distal end 102 of the tool 100 is placed over the skin so that the notch defined by the open region 103 is aligned with the desired exit point, at the location 116. The free, previously undermined skin can be slightly laterally maneuvered, as necessary, to ensure that the location 116 is correctly aligned with the desired trajectory of the suture passer. The sharp tip 88 can then safely penetrate the skin and pass through the notch without a risk of prick injury. Downward forces applied by the distal end 102 of the tool 100 also serve to oppose the exiting force of the tip 88 as it exits the subcutaneous tissue and the skin.

Figure 26:
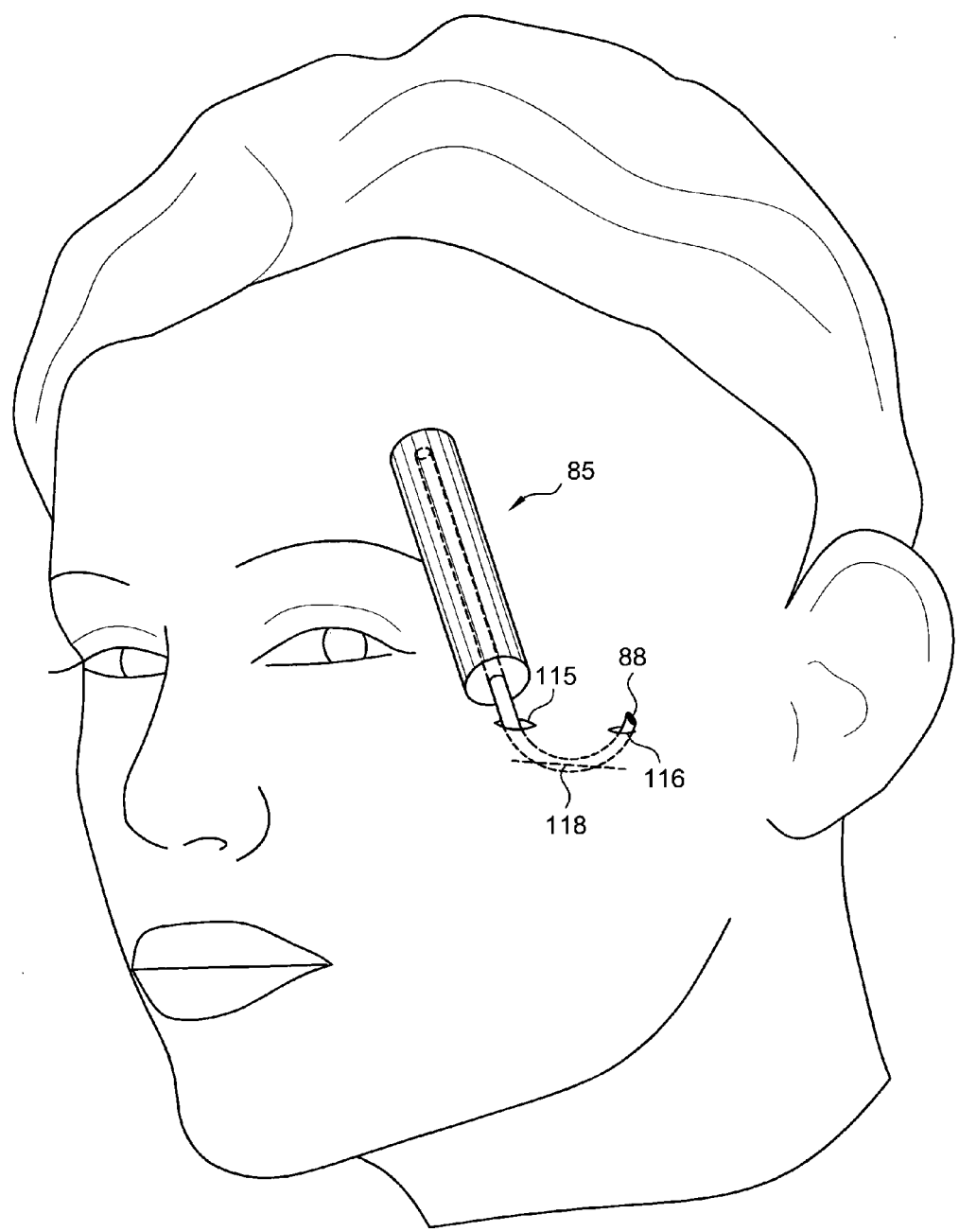

FIG. 26 shows the cannula 87 of the suture passer following the completion of its trajectory through the facial tissue. The tip 88 has then fully exited the skin, at the location 116. As an alternative, the tool shown in FIG. 18 can provide a similar result by using the curved needle 91 to pass a suture received by the eyelet 92 of the tip 93 through the exit location 116, preferably with the assistance of the tool 100.

Figure 27:
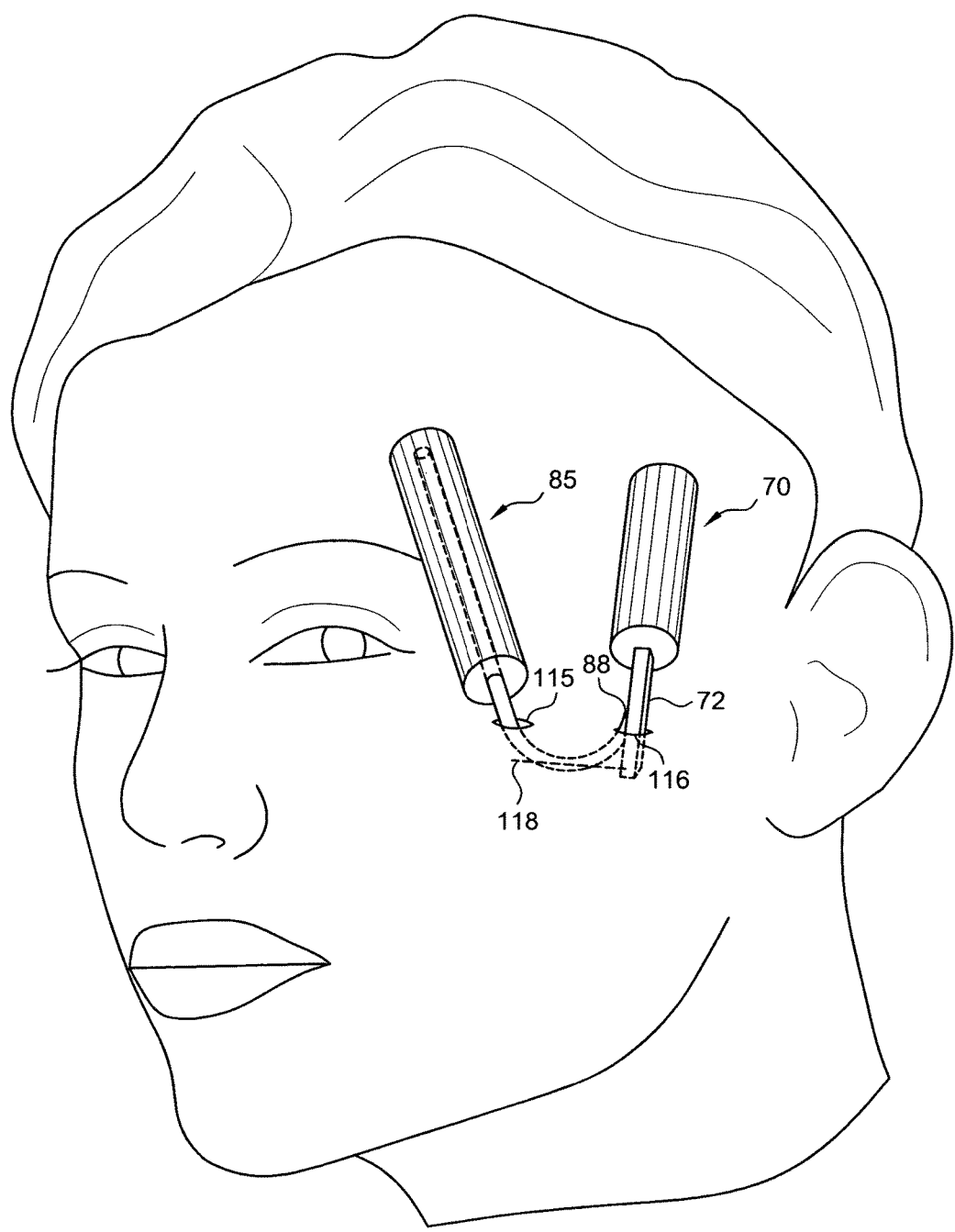

Referring next to FIG. 27, the narrow scalpel shown in FIG. 14 is used to make an incision adjacent to the exiting tip 88 of the ligature passer, at 116. This incision serves to widen the puncture produced by the tip 88, for later receiving the elongate member 6 of the fixture 1 as will be described more fully below. Making an incision adjacent to the cannula 87 of the ligature passer ensures that the exiting puncture and the incision located at 116 are contiguous and that there is no unwanted connective tissue between them.

Figure 28:
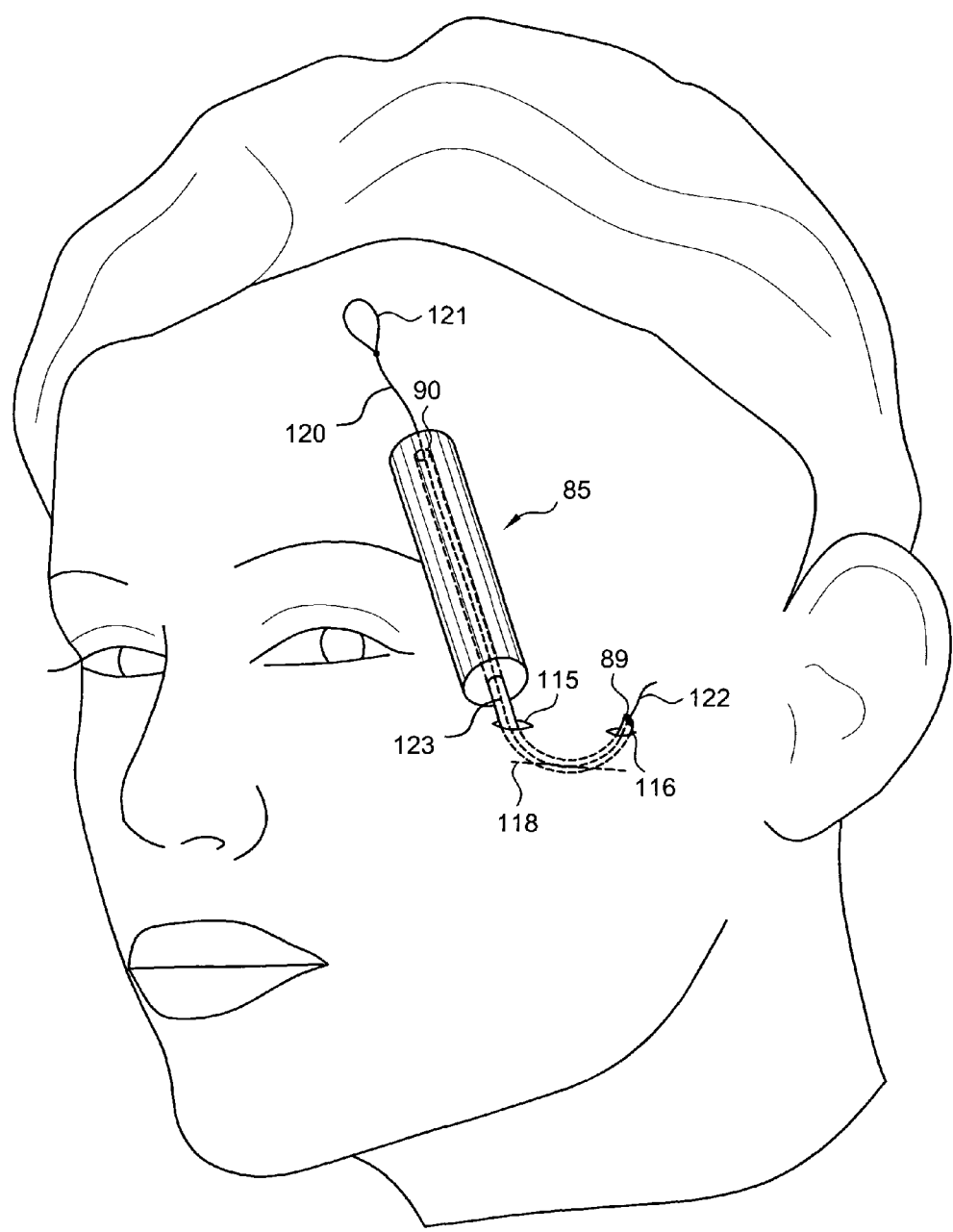

In FIG. 28, a suture 120 having a terminating loop 121 is shown threaded through the tool 85 and exiting from the aperture 89 of the tip 88. This suture is provided for temporary use, and will subsequently be used to drag a second, sling-forming suture through an anchoring path which will be described more fully below. A metallic suture is preferably used as the suture 120 because such a suture can resist being cut by sharp devices, in subsequent steps of the procedure. As an alternative, conventional suture material can be used, provided care is used to prevent cutting of the suture. A non-looped suture can also be used. However, as will be described below, the use of a suture without a loop will require the suture to be tied temporarily to the suture forming the sling before dragging the sling-forming suture through its anchoring pathway.

Figure 29:
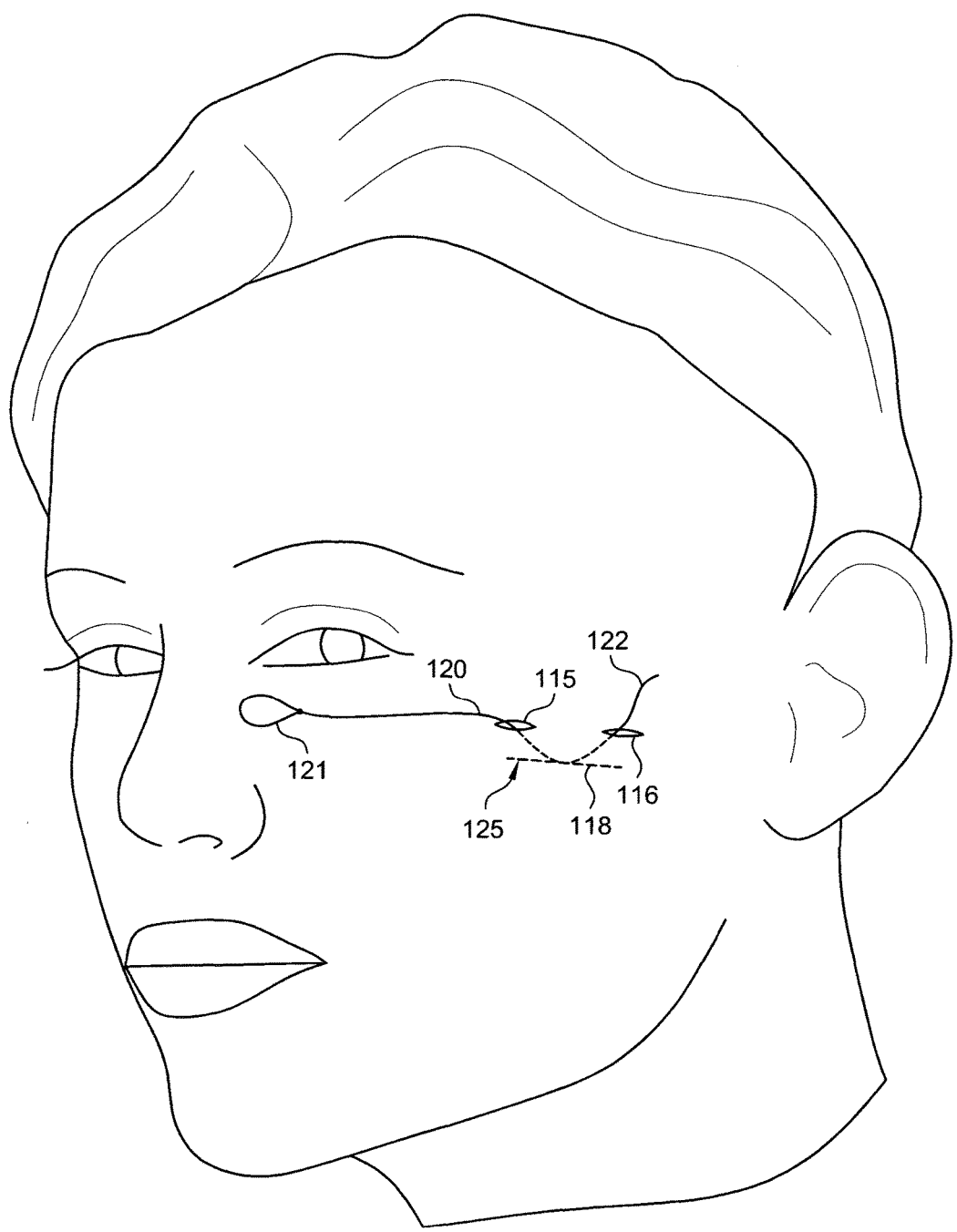

FIG. 29 shows the suture 120 positioned in place after the ligament passer has been removed. Following this, the loop 121 and the end 122 of the suture 120 exit the skin at the locations 115, 116, and center portions 123 of the suture 120 pass through the periosteum, at 125.

Figure 30:
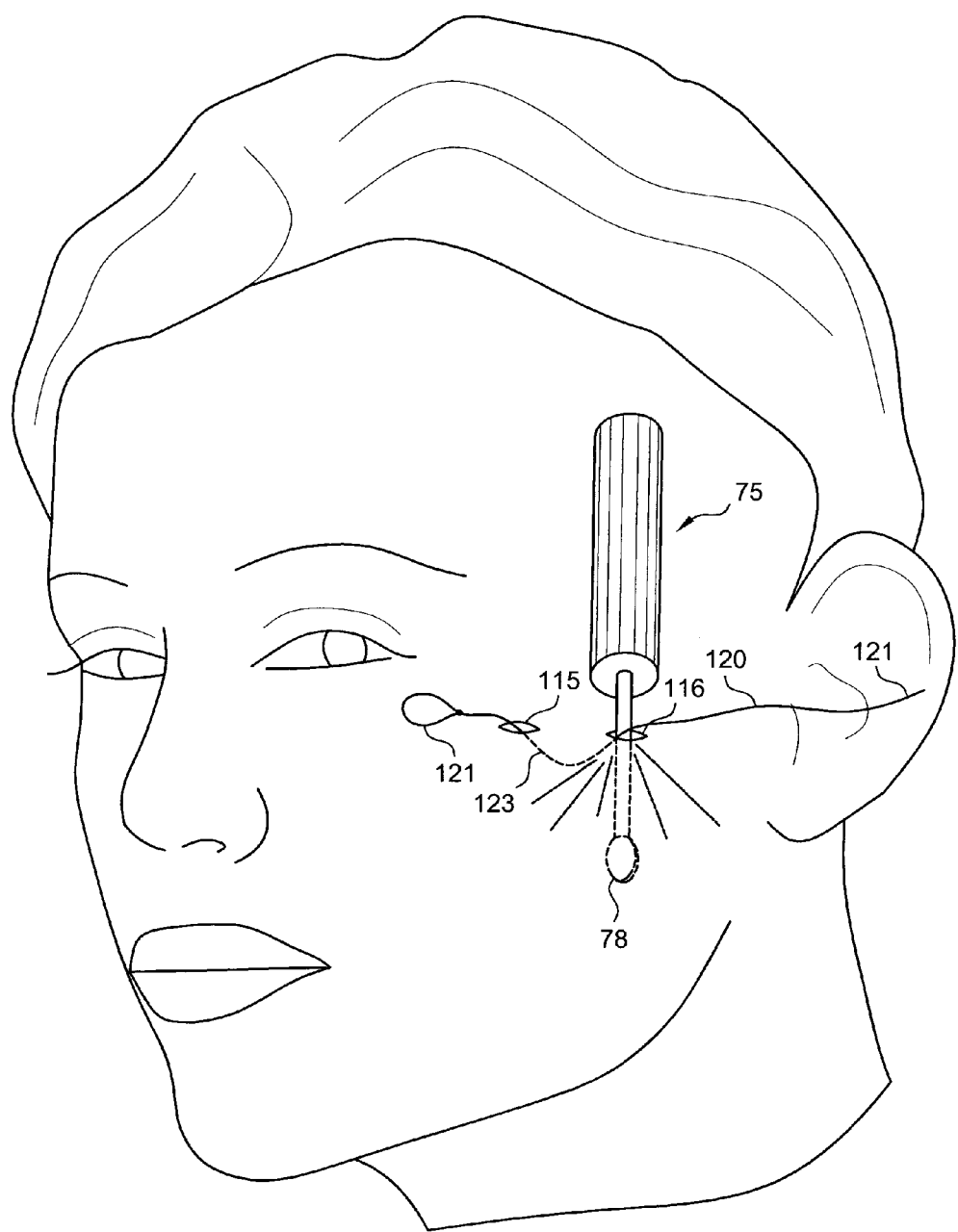

Referring now to FIG. 30, the dissecting tool 75 of FIG. 15 is shown entering the second incision 116 and undermining an additional region surrounding the incision 116. Such additional undermining again serves to separate layers of subcutaneous tissue in the region of the incision, and to relieve portions of the fat layer, as may be required for cosmetic reasons.

Figure 31:
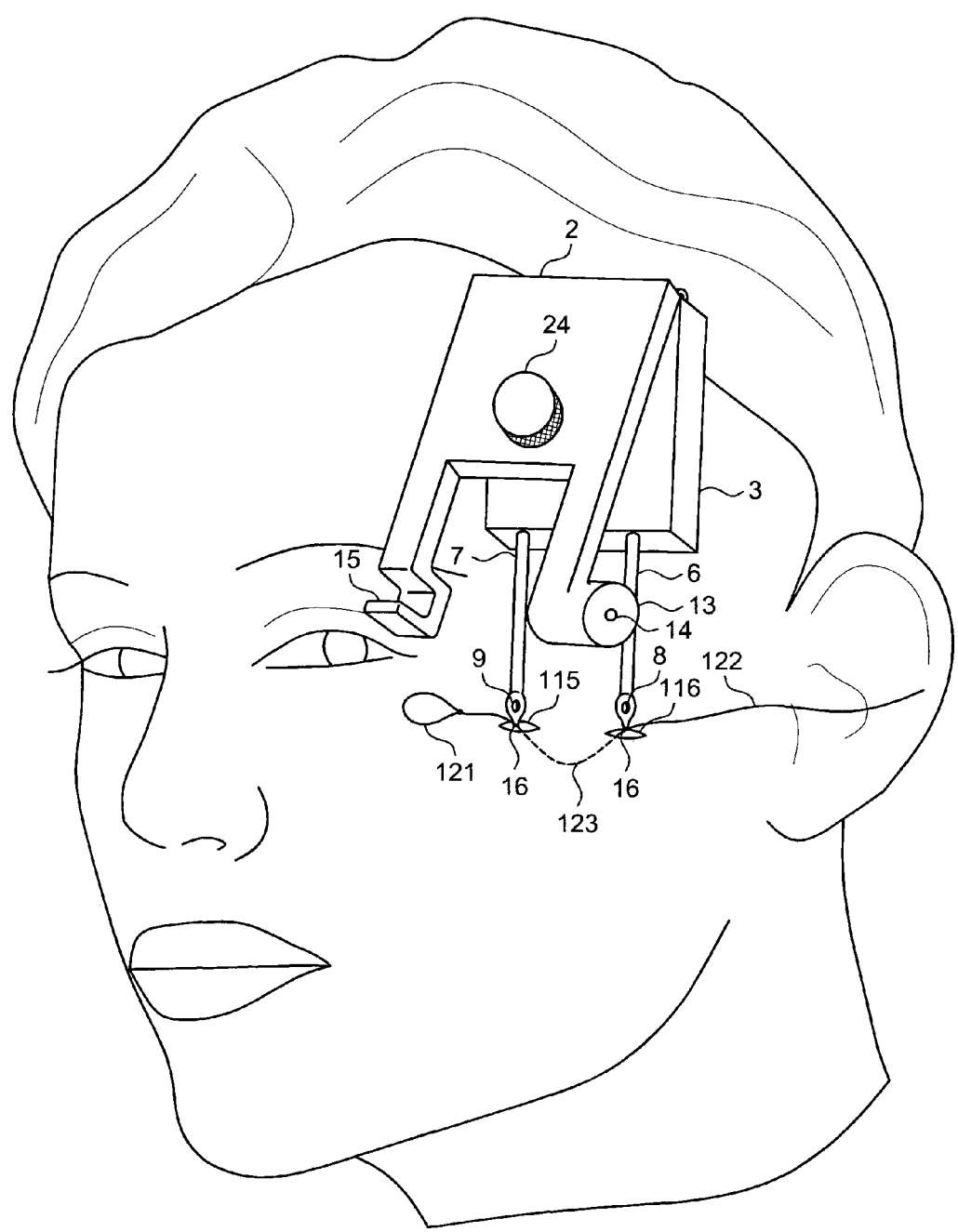

In FIG. 31, the fixture 1 is shown just prior to use, positioned for entering the incisions 115, 116. The upper body 2 and the lower body 3 are separated so that the guide 13 and the guard 15 of the upper body 2 are in an open position relative to the elongate members 6, 7 of the lower body 3, and so that the guide 13 and the guard 15 of the upper body 2 do not obscure the procedure and do not impinge on facial tissue. The elongate members 6, 7 of the fixture 1 have a fixed spacing which corresponds to the spacing of the incisions 115, 116, and are shown ready for insertion into the incisions 115, 116 until the elongate members 6, 7 reach the desired depth inside the subcutaneous tissue. If the fixture 30 of FIG. 6 is used, instead of the fixture 1, the spacing between the elongate members 6, 7 can be adjusted to match the spacing between the incisions 115, 116 by operation of the thumb screw 32.

Figure 32:
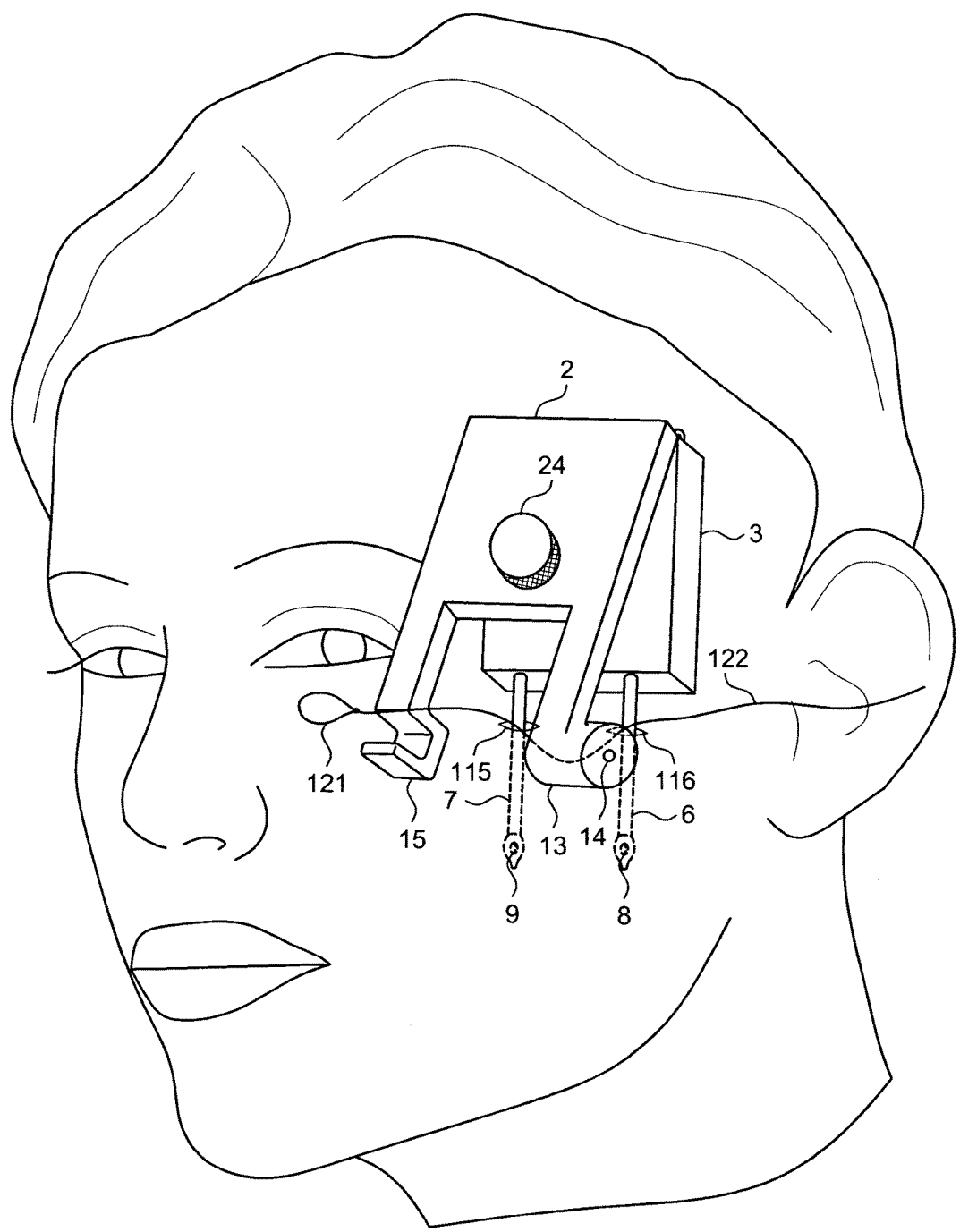

FIG. 32 shows the elongate members 6, 7 of the fixture 1 following entry into the incisions 115, 116, and penetrating the subcutaneous tissue to the intended depth (location). When using a fixture having elongate members with a fixed spacing, the undermined skin can be manually manipulated to cause the distance between the incisions 115, 116 to match the spacing of the elongate members. Manual manipulation of the skin is not required when using a fixture having elongate members with an adjustable spacing, provided the correct spacing of the elongate members has been established as previously indicated.

Figure 33:
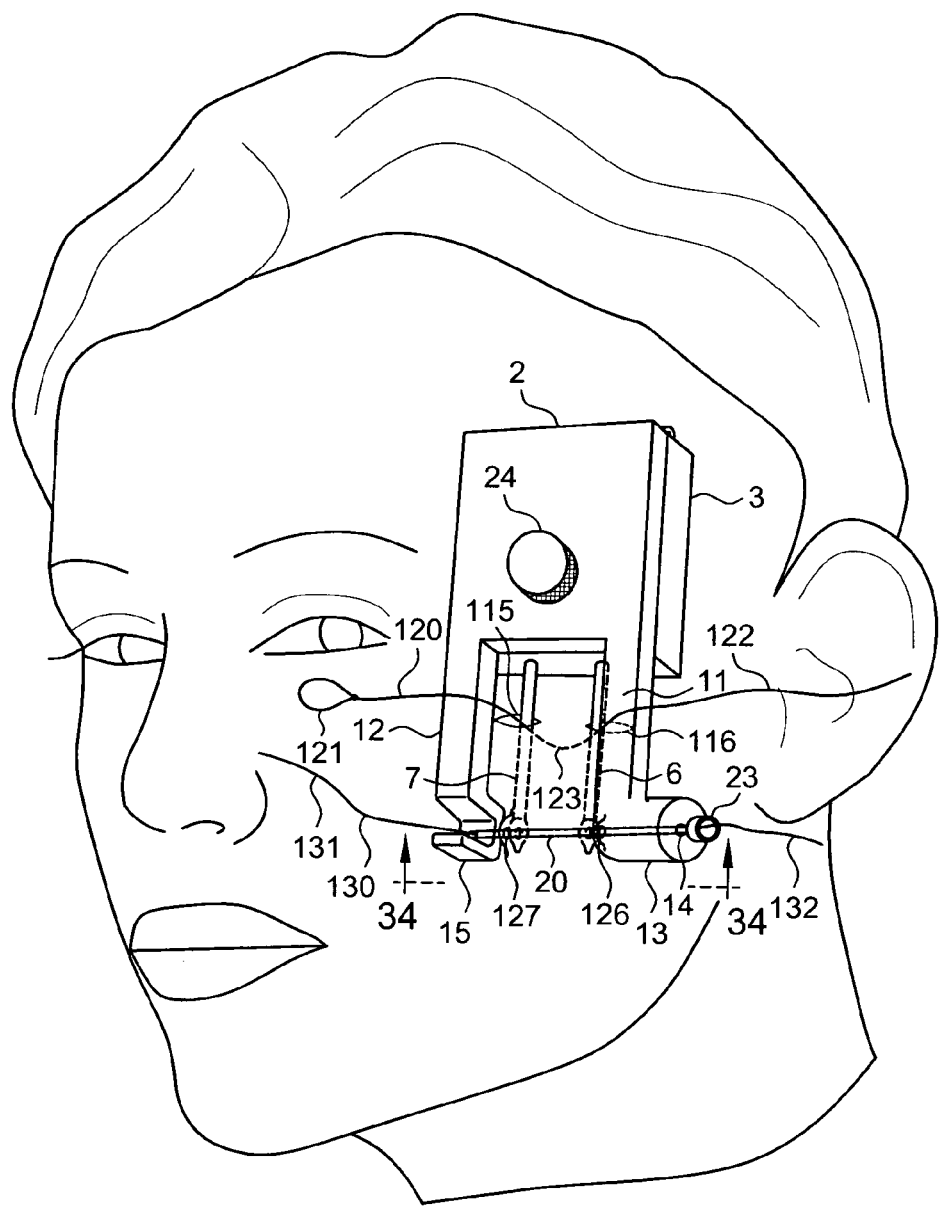

Following penetration of the elongate members 6, 7 to their desired depth (location), the upper body 2 and the lower body 3 are clamped together, using the thumb screw 24, positioning the guide 13 and the guard 15 of the upper body 2 over the skin, as shown in FIG. 33. As a result, the guide 13 and the guard 15 of the upper body 2 are brought into position against the skin, and are aligned with the centerline 21 of the subcutaneous eyelets 8, 9 of the elongate members 6, 7, as previously described.

Figure 34:
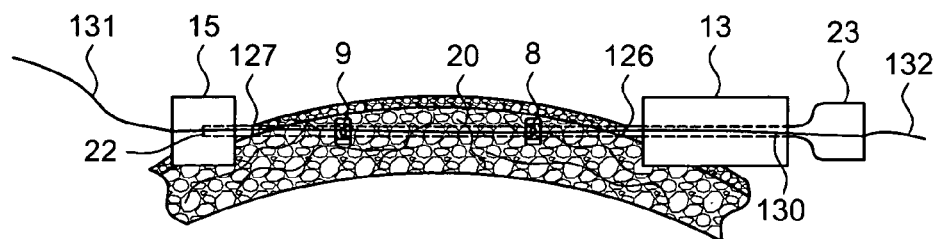

As is further shown in FIG. 34, the suture passing cannula 20 shown in FIG. 1 is inserted into the aperture 14 of the guide 13. Further advancement of the cannula 20 causes the tip 22 to penetrate the skin, at a puncture 126, passing subcutaneously beneath the skin and through the eyelets 8, 9 of the elongate members 6, 7. Further advancement of the cannula 20 again causes the tip 22 to penetrate the skin, exiting from a puncture 127 and entering the guard 15 to prevent prick injury to the user of the fixture 1. After the cannula 20 has been fully inserted into the guide 13 and guard 15 of the fixture 1, a suture 130 is threaded completely through the cannula 20. Such threading of the suture 130 can be performed from either end of the cannula 20, and can be assisted by providing the cannula 20 with a hub, as previously described.

In FIGS. 33 and 34, a conventional suture 130 has been threaded through the suture passer (the cannula 20). As an alternative, a suture having tissue-engaging structures such as the modified portion 63 of the suture 60 shown in FIG. 12 or the modified portions 63 of the suture 65 shown in FIG. 13 can be used. As a further alternative, a suture (with or without tissue-engaging structures) having an attached needle can be used instead of the suture passer. However, in such cases, the needle must be cut off after passing through the placement apparatus.

FIG. 34 shows a cross-section through the cheek of the patient. Illustrated is a thin layer of skin and a thick layer of subcutaneous tissue. The cannula 20 is seen passing through the aperture 14 of the guide 13, through the puncture 126 entering the skin, through the eyelets 8, 9 of the elongate members 6, 7, through the puncture 127 exiting the skin, and into the guard 15 so that the sharp tip 22 of the cannula 20 comes to rest inside the guard 15.

Figure 35:
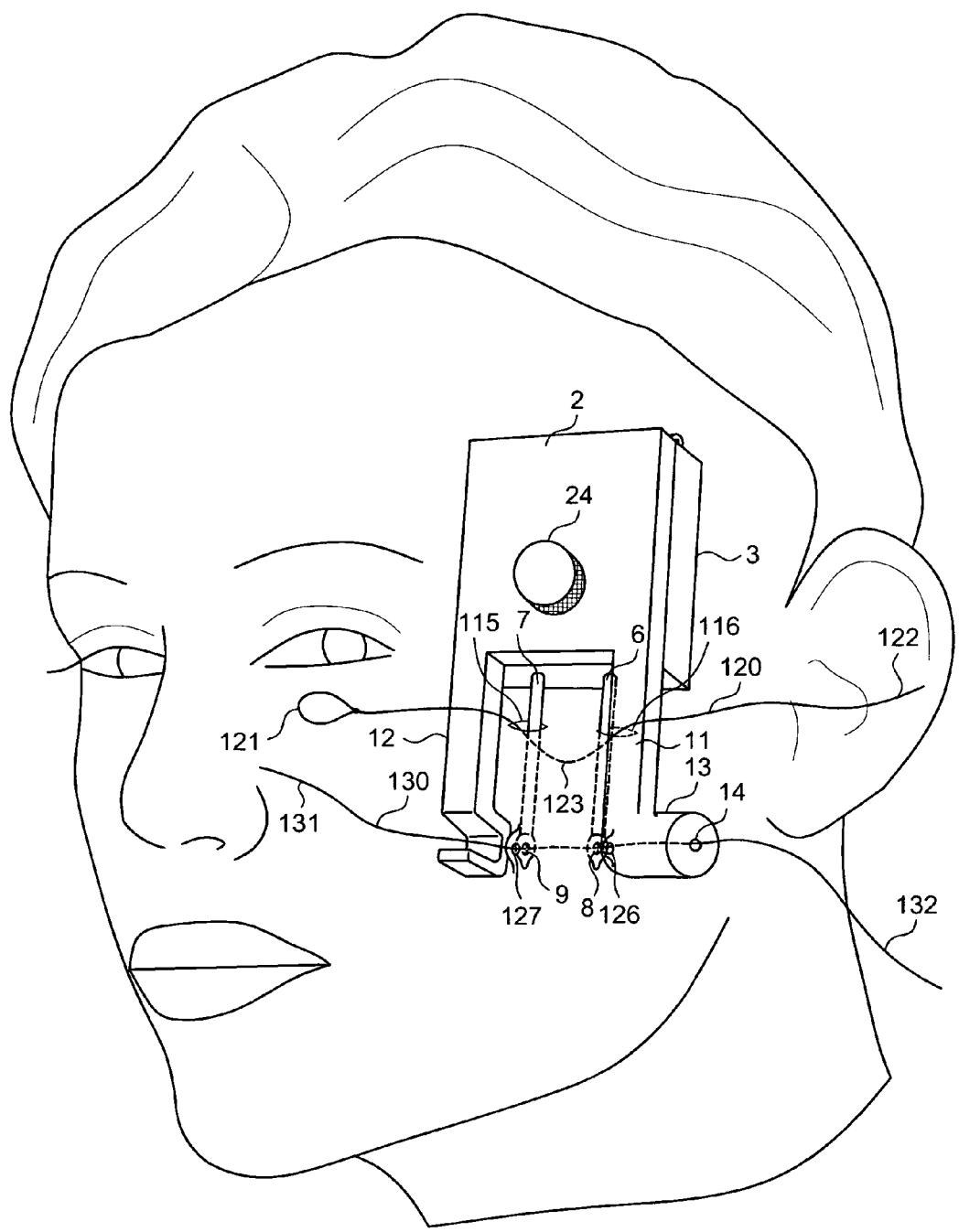

Referring to FIG. 35, the cannula 20 is then retracted and removed from the fixture 1, while grasping a free end 131 of the suture 130. As a result, the suture 130 is left in place, extending from the punctures 126, 127 and beneath the skin, following removal of the cannula 20. At this point, the suture 130 is also received within the guide 13 and the guard 15 of the fixture 1.

Figure 36:
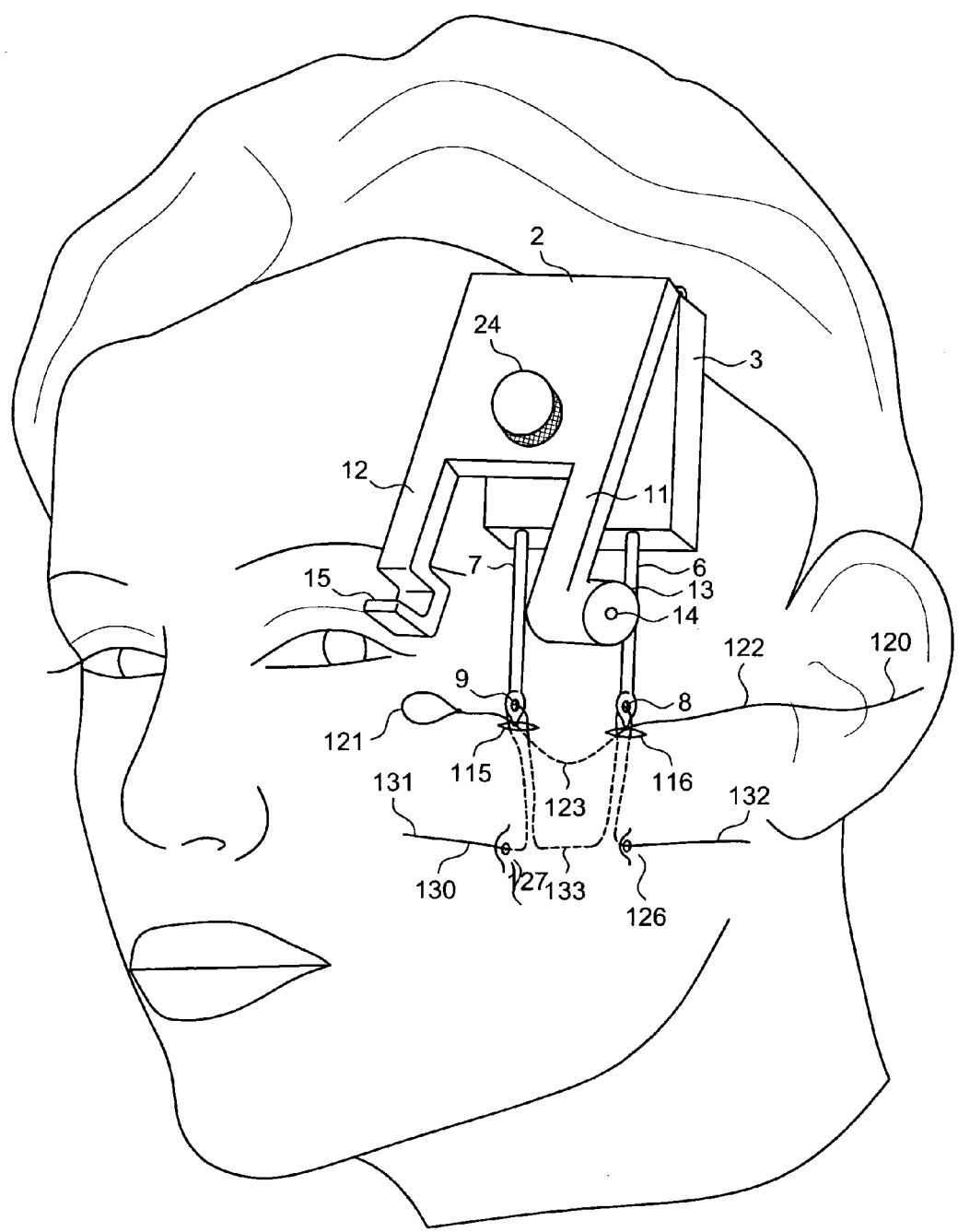

Referring to FIG. 36, the thumb screw 24 is then released, allowing the upper body 2 to swing away from the lower body 3. This serves to open the fixture 1 and to release the fixture 1 from against the skin, in this way facilitating removal of the fixture from the patient. The suture 130 is also in this way released from the guide 13 and from the guard 15. As a result, the lower body 3 and the elongate members 6, 7 are released for withdrawal from the incisions 115, 116. Retraction of the elongate members 6, 7 causes the suture 130 which is engaged by the eyelets 8, 9 to be pulled upwardly, eventually pulling the engaged portions of the suture 130 through the incisions 115, 116.

Figure 37:
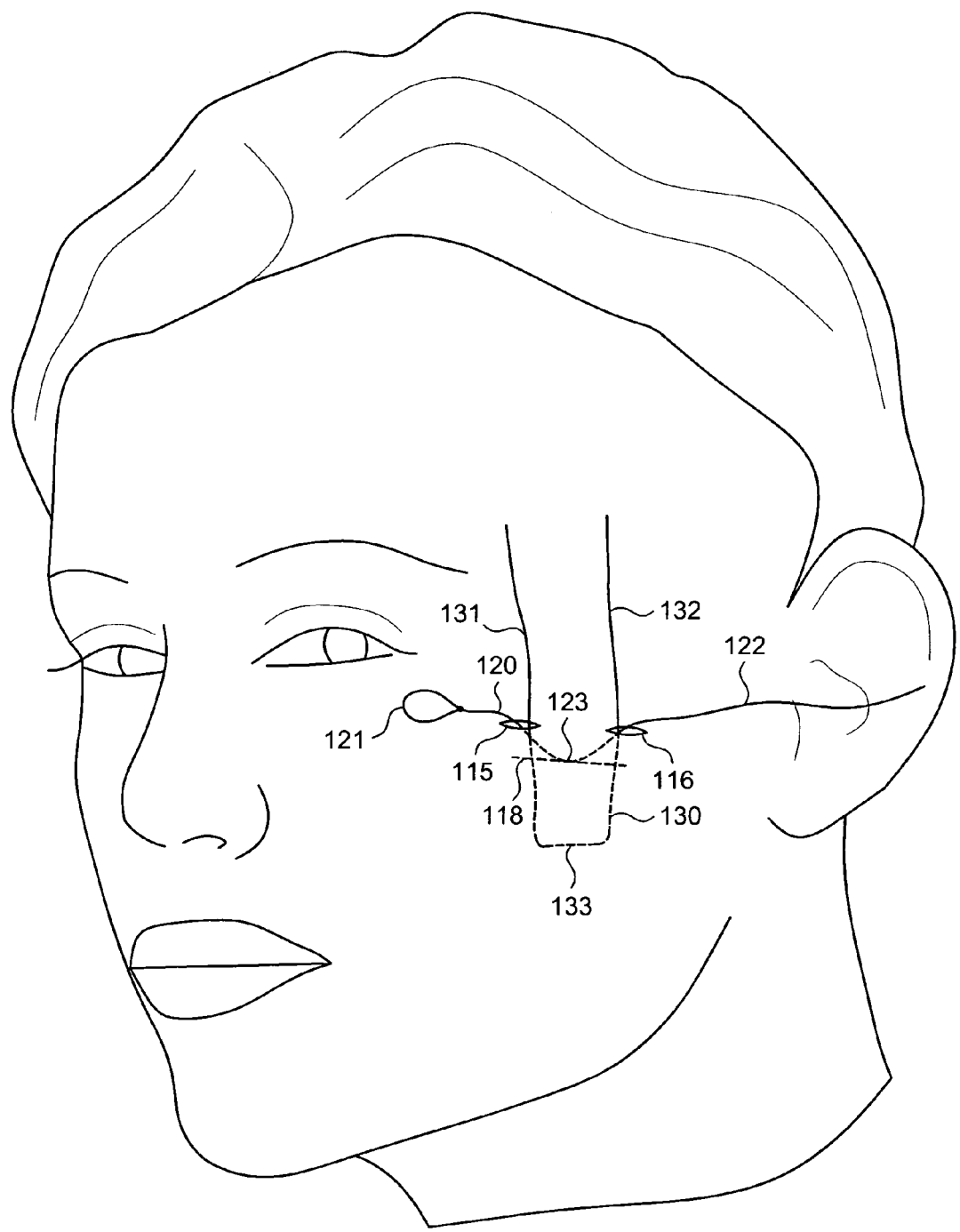

In the intermediate position shown in FIG. 36, the ends 131, 132 of the suture 130 remain extended from the punctures 126, 127, and the center section 133 of the suture 130 remains in position between the puncture points 126, 127 resulting from the engagement of subcutaneous tissue shown in FIG. 34. After the fixture 1 has been completely withdrawn, the ends 131, 132 of the suture 130 will be pulled through and will freely extend from the incisions 115, 116, following release from the eyelets 8, 9 of the elongate members, and the center section 133 of the suture 130 will remain in position between the puncture points 126, 127, as is shown in FIG. 37. As a result, the suture 130 develops a U-shaped sling 135 comprised of the ends 131, 132 and center section 133 of the suture 130, and which forms a halter for supporting the lower, subcutaneous tissue engaged by the center section 133. The suture 120 also remains in place, extending from the incisions 115, 116.

Figure 38:
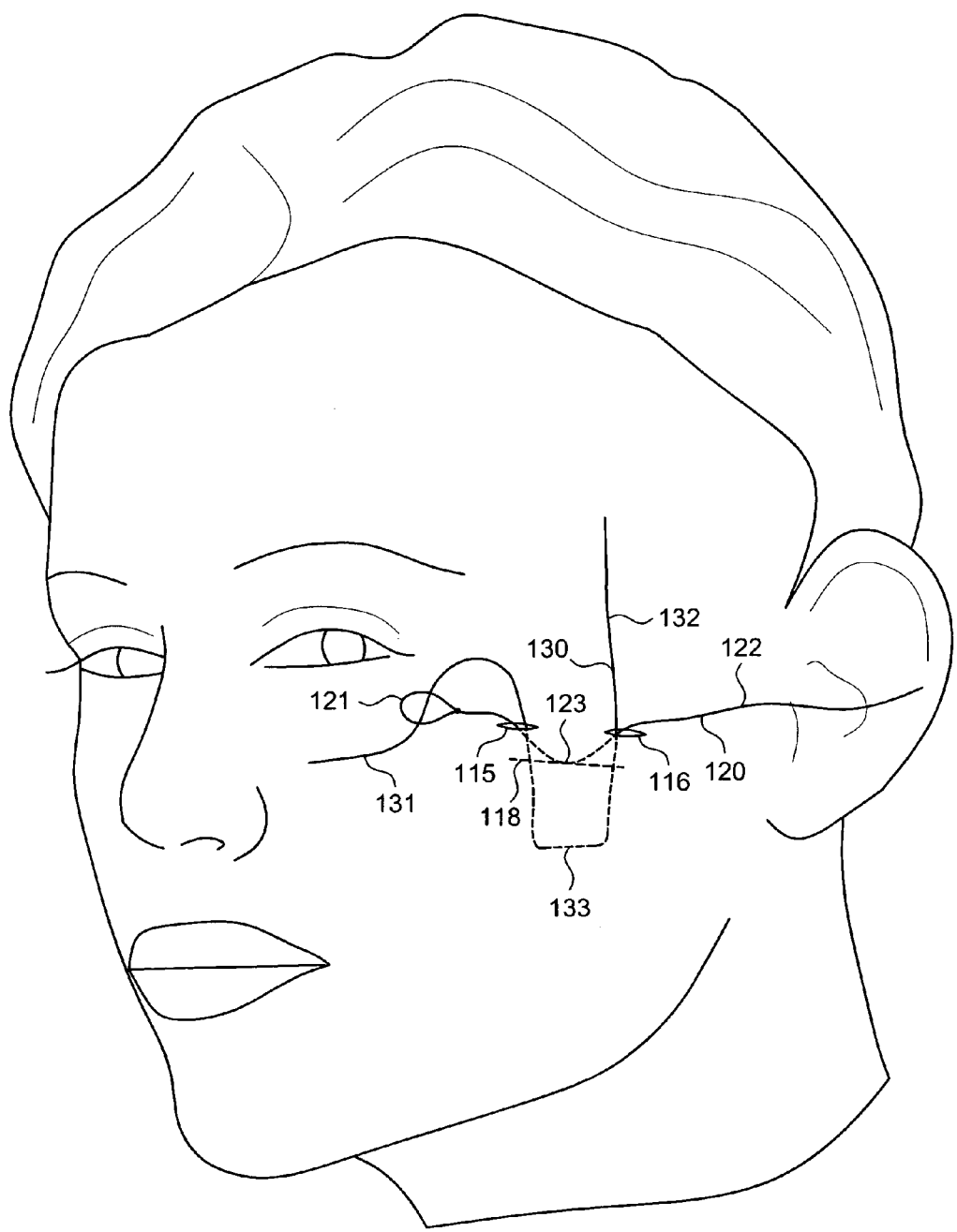
Figure 39:
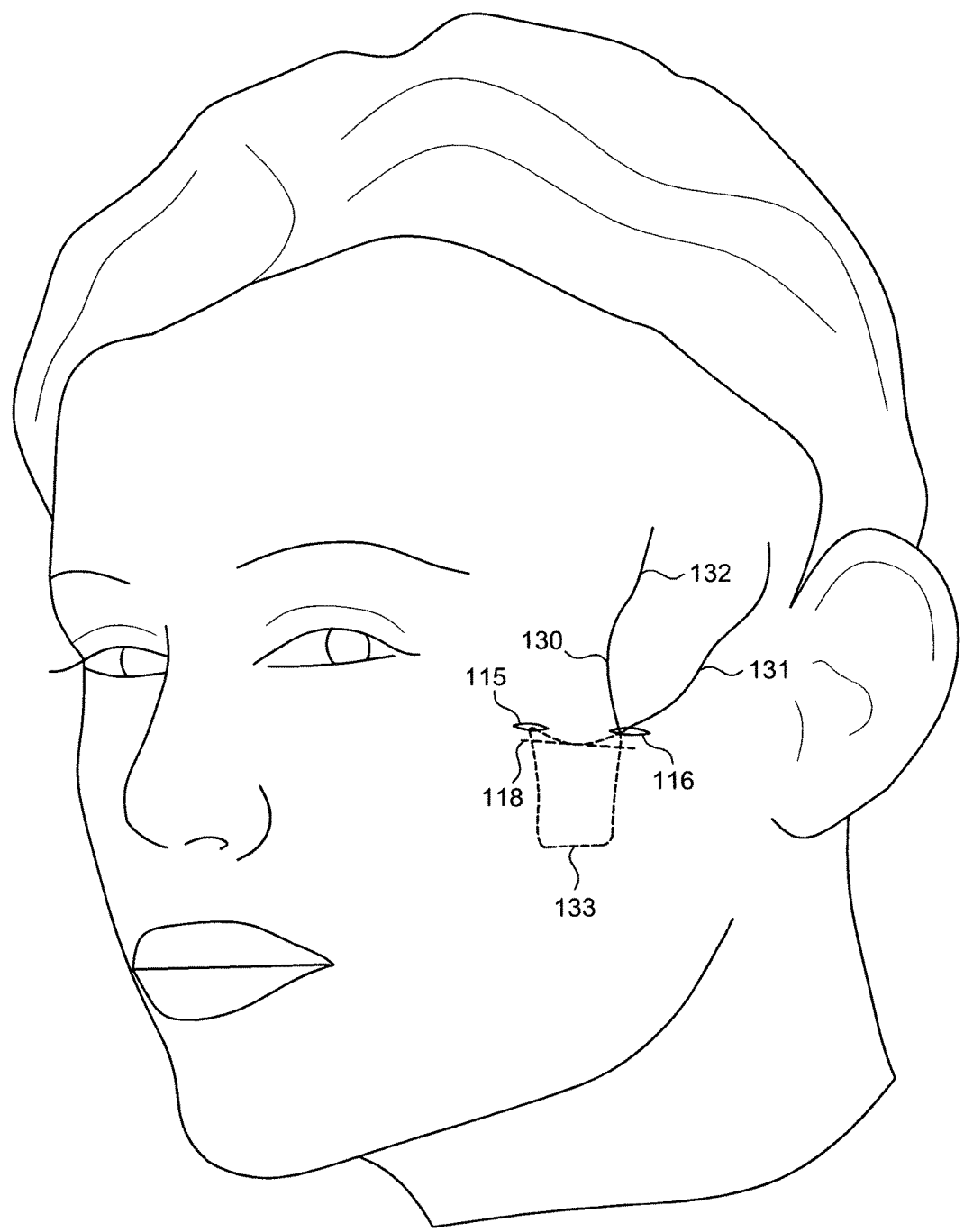

Referring now to FIG. 38, the end 131 of the lower suture 130 is threaded through the loop 121 of the upper suture 120. Following this, the end 122 of the upper suture 120 is retracted, causing the end 131 of the lower suture 130 to be pulled through the incision 115, and then through the incision 116. The loop 121 of the upper suture 120 is then removed from the end 131 of the lower suture 130, leaving the ends 131, 132 of the suture 130 adjacent to each other, as shown in FIG. 39.

Retraction of the suture 120 causes the engaged end 131 of the suture 130 to pass through the periosteum or ligament of the zygomatic arch 118 previously engaged by the suture 120. The ends 131, 132 of the remaining suture 130 are then drawn, and appropriately tensioned for the amount of lift which is desired for the procedure being performed. Upon achieving the appropriate tension, the ends 131, 132 are then tied together, and the knots are embedded within the subcutaneous tissue, completing the surgical procedure. The incisions 115, 116 and the punctures 126, 127 are at this point clear of all structures, for appropriate closure and healing.

As previously indicated, numerous variations of the above-described surgical procedure are possible. One such variation makes use of the tissue-engaging suture 60 shown in FIG. 12, in place of a conventional suture, to form the sling 135 shown in FIGS. 37 to 39. Use of the suture 60 serves to position the modified portion 63 of the suture 60 within the subcutaneous tissue which is best shown in FIG. 34, providing additional reinforcement along the center section of the suture 60 which includes the modified portion 63.

Figure 40:
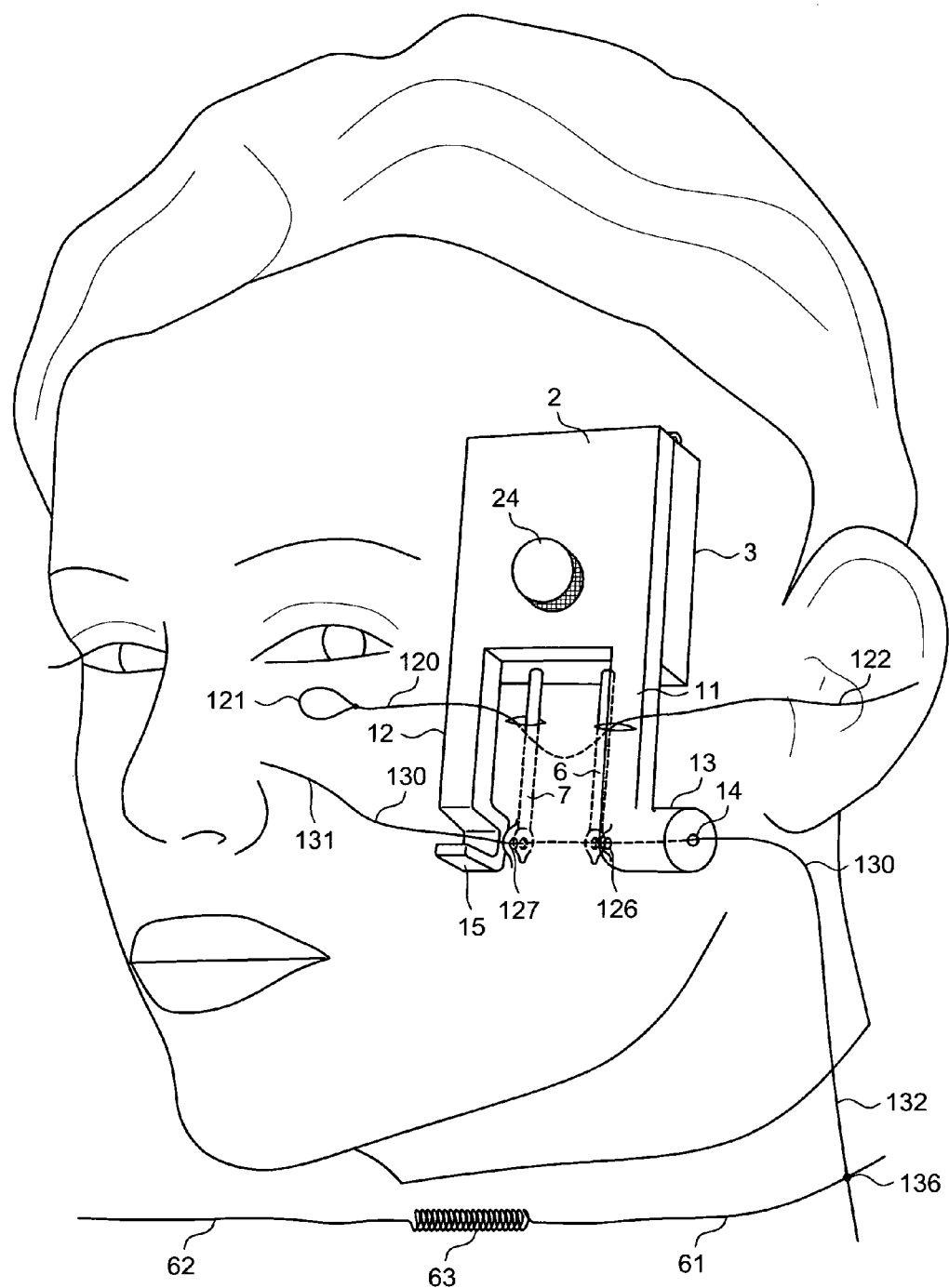
FIGS. 40 and 41 are sequential illustrations showing modification of the surgical procedure for use of the suture shown in FIG. 12.

FIG. 40, which substantially corresponds to FIG. 35, illustrates use of the suture 60 in a surgical procedure. In such a procedure, the suture 130 will have been threaded through the cannula 20 (which can be left in place in the fixture 1 or removed from the fixture 1), leaving the suture 130 in the position shown. The suture 60 (including the modified portion 63) is then tied to the end 132 of the suture 130, at 136, so that retraction of the suture 130 can draw the suture 60 through the fixture 1, in place of the suture 130.

Figure 41:
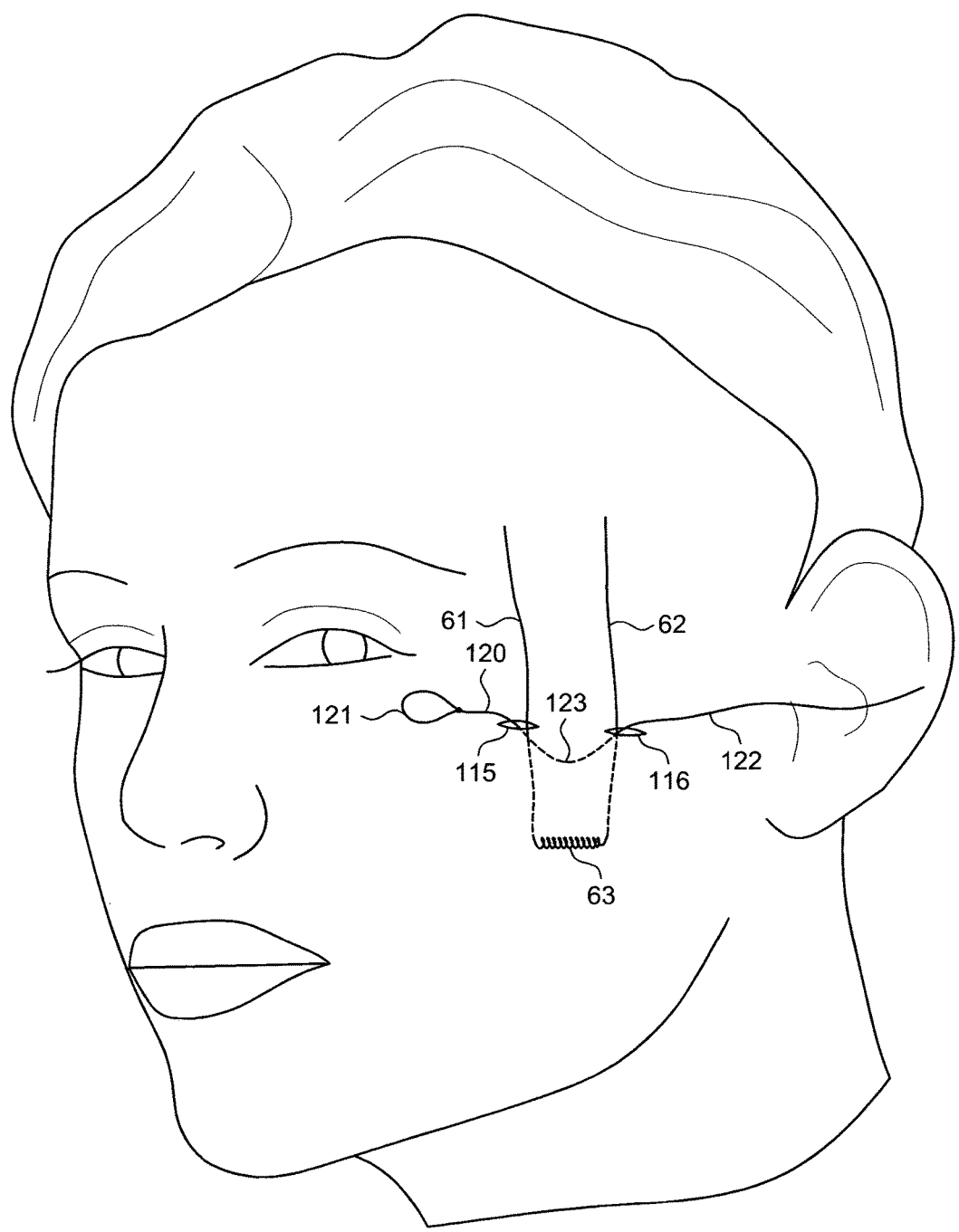

Referring to FIG. 41, the modified portion 63 of the suture 60 is then positioned as shown to form a center section similar to the center section 133 of the sling 135 developed when using the suture 130, and the remainder of the surgical procedure continues, as previously described, making use of the suture sections 61, 62 of the suture 60 in place of the ends 131, 132 of the suture 130.

Another variation of the above-described surgical procedure makes use of the fixture 30 shown in FIG. 6 (or, alternatively, the fixture 30' shown in FIG. 7 or the fixture 30" shown in FIG. 8). Use of the fixture 30 is substantially similar to use of the fixture 1 shown in FIGS. 1 to 4, with the added feature that the spacing between the elongate members 6, 7 can be adjusted to exactly match the spacing of the facial incisions 115, 116 prior to use of the fixture 30. However, instead of opening and closing the fixture 1, using the thumb screw 24, the arms 28, 29 of the fixture 30 are preferably removed from the body sections 31a, 31b prior to insertion of the elongate members 6, 7 into the incisions 115, 116, and when removing the elongate members 6, 7 from the incisions 115, 116, and are preferably attached to the body sections 31a, 31b following insertion of the elongate members 6, 7 into the incisions 115, 116, for proceeding with the desired surgical procedure. The removable arms 28, 29 of the fixture 30 (or the fixtures 30', 30") which support the guide 13 and the guard 15 can be assembled or removed during the surgical procedure using the knurled screws 33.

Another variation of the above-described surgical procedure makes use of the fixture 35 shown in FIGS. 9 and 10. Use of the fixture 35 is substantially similar to use of the fixture 1 shown in FIGS. 1 to 4, subject to the variations which follow.

Figure 42:
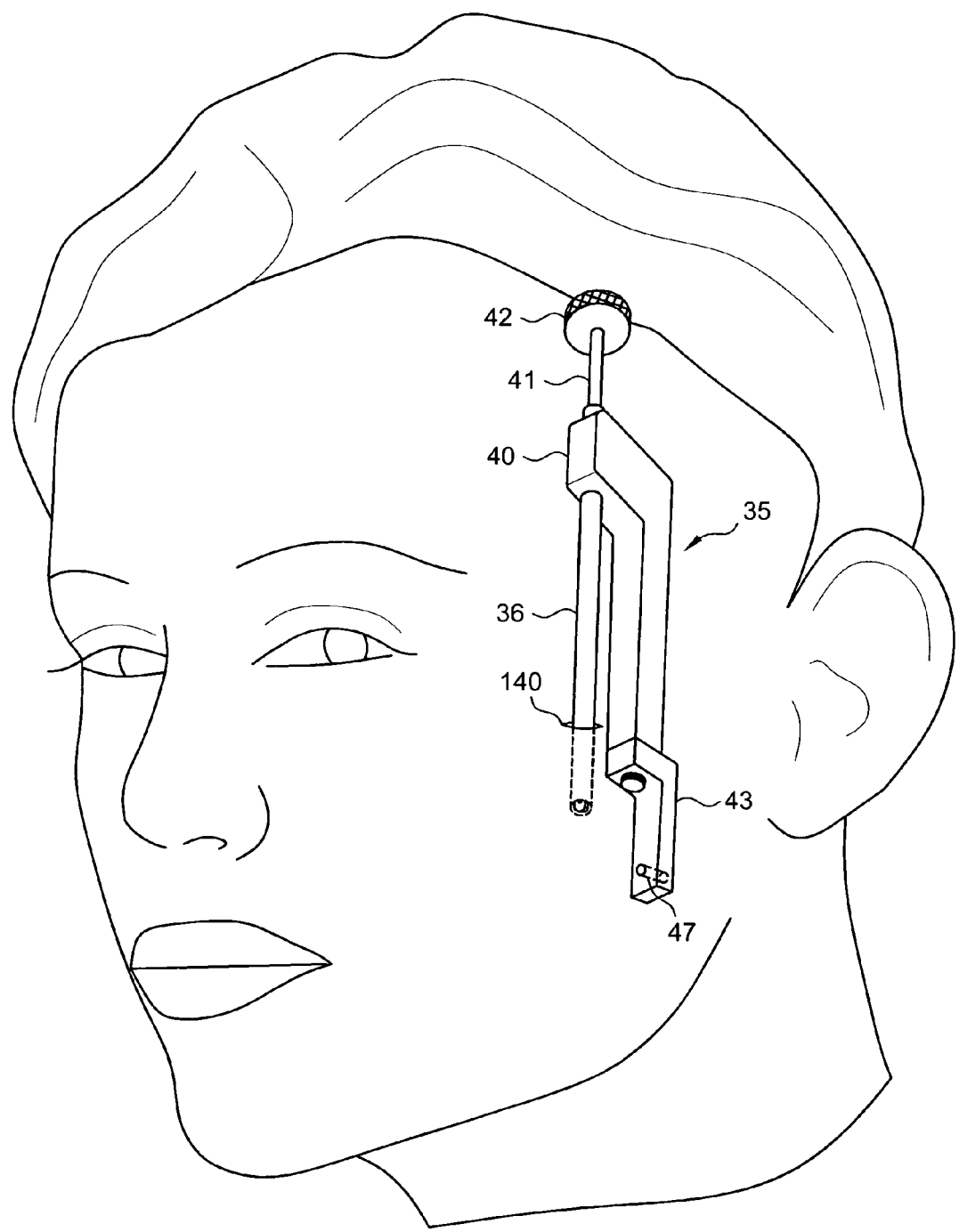
FIGS. 42 through 45 are sequential illustrations showing modification of the surgical procedure for use of the alternative embodiment fixture shown in FIGS. 9 and 10.

Referring to FIG. 42, an incision is made at a single location 140 which can be at the zygomatic arch, or above the hairline, in place of the incisions previously made at the locations 115, 116. When using the fixture 35, undermining is not recommended within 1 cm of the location for receiving the bottom of the suture sling which will be described more fully below.

Initially, the extensions 38, 39 associated with the single elongate member 36 of the fixture 35 will be retracted into the hollow tube which forms the elongate member 36. In this initial configuration, the elongate member 36 of the fixture 35 is inserted into the incision 140, to a depth of penetration which is approximately 1 cm from the location for the bottom of the suture sling which is to be formed. The guide 43 is assembled onto the handle 40 using the knurled screw 44, before or after insertion of the elongate member 36, readying the fixture 35 for continuation of the procedure.

Figure 43:
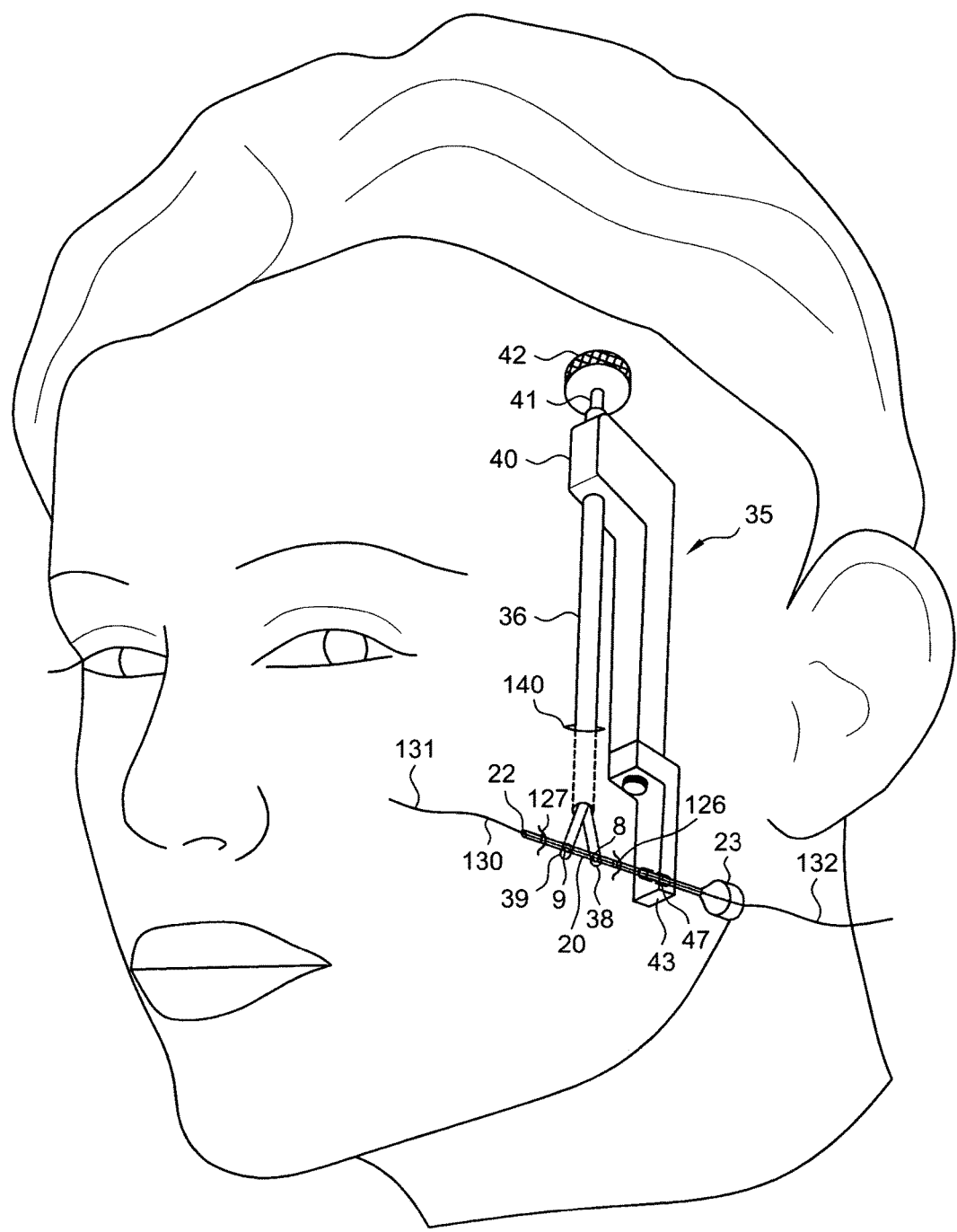

Referring to FIG. 43, the shaft 41 is advanced into the hollow elongate member 36, by pushing on the knob 42, causing the extensions 38, 39 to deploy from the distal end of the elongate member 36 and to further penetrate into the subcutaneous tissue. As a result, the eyelets 8, 9 of the extensions 38, 39 are brought into alignment with the centerline 21 which extends through the aperture 47 formed in the guide 43, as previously described. The cannula 20 can then be inserted into the aperture 47 formed in the guide 43 of the fixture 35, passing through the aperture 47 of the guide 43, through the puncture 126 for entering the skin, through the eyelets 8, 9 of the extensions 38, 39, and through the puncture 127 for exiting the skin. A suitable suture 130 (either with or without a thickened section 63, and with or without an attached needle) can then be threaded through the cannula 20, so that the ends 131, 132 of the suture 130 extend from the punctures 126, 127, and so that the thickened section 63 (if used) is located between the eyelets 8, 9, as previously described. The cannula 20 is then removed from the fixture 35. As an alternative, a suture attached to a needle can be similarly employed, without the use of a cannula 20, if desired.

Figure 44:
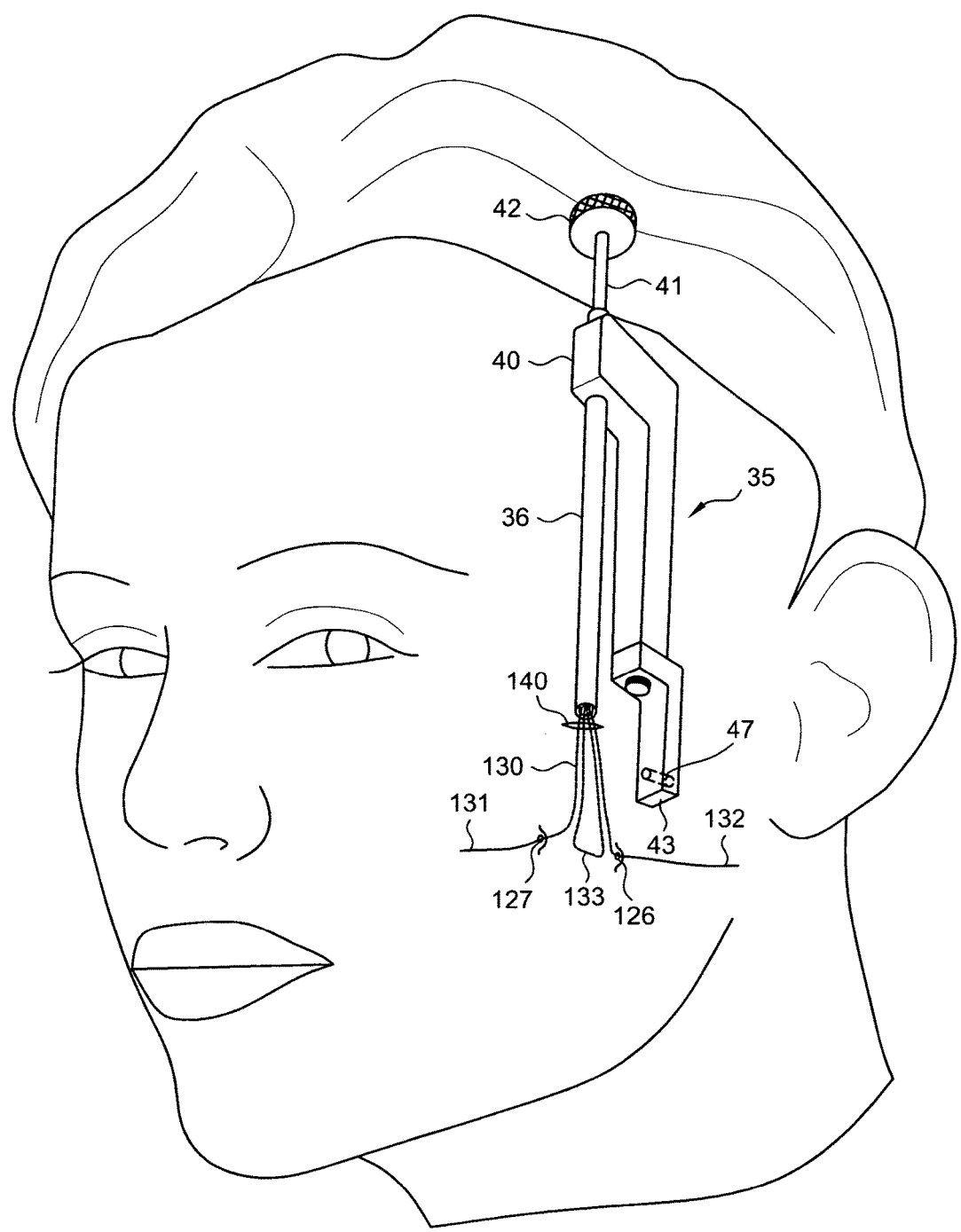
Figure 45:
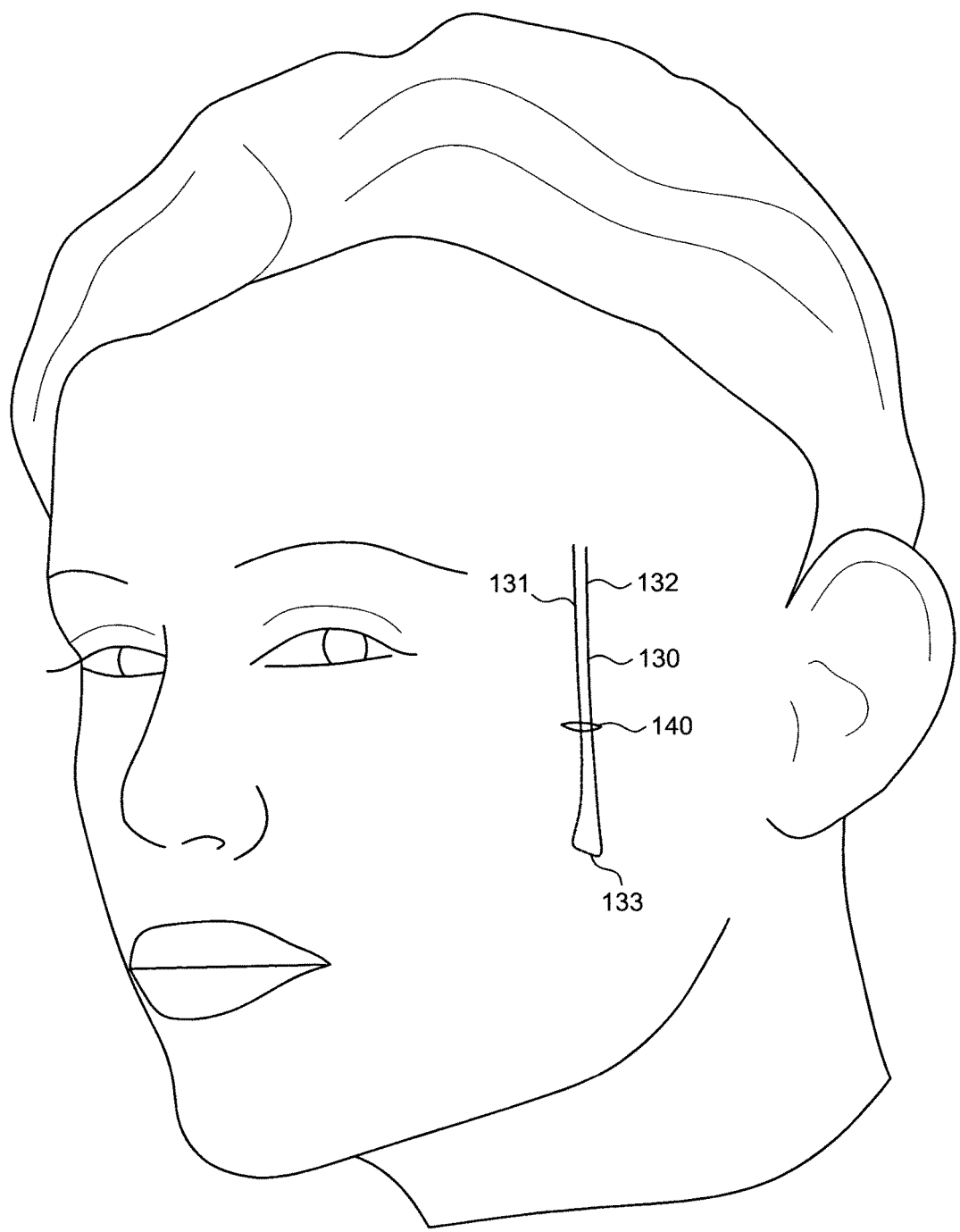

Referring to FIG. 44, the extensions 38, 39 are then retracted into the elongate member 36, by retracting the shaft 41. As a result, the suture 130 engaged by the eyelets 8, 9 of the extensions 38, 39 will also be drawn into the elongate member 36. The fixture 35 is then withdrawn from the incision 140, in turn drawing the ends 131, 132 of the suture 130 through the punctures 126, 127, and through the incision 140, as shown in FIG. 45. As a result, the ends 131, 132 of the suture will extend from the incision 140, and the center section 133 of the suture 130 will remain in position between the puncture points 126, 127, and within the subcutaneous tissue, as previously described. The resulting sling can then be tensioned to lift the tissue, and then anchored, as previously described, completing the desired surgical procedure.

Another variation of the above-described surgical procedure makes use of the fixture 50 shown in FIG. 11. Use of the fixture 50 is once again substantially similar to use of the fixture 1 shown in FIGS. 1 to 4, subject to the variations which follow.

Figure 46:
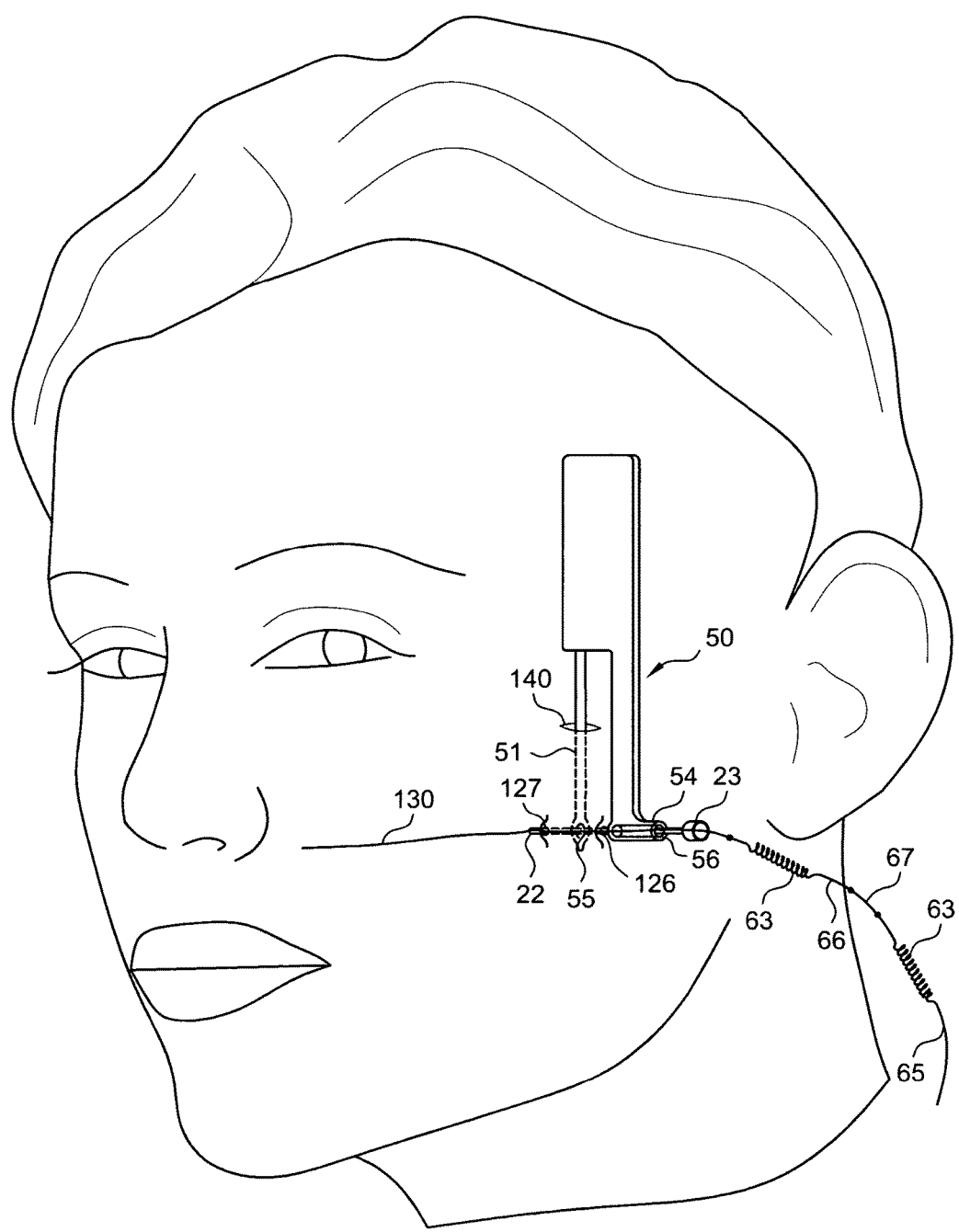
FIGS. 46 through 49 are sequential illustrations showing modification of the surgical procedure for use of the alternative embodiment fixture shown in FIG. 11.

Referring to FIG. 46, a single incision is again made at a location 140, which can be at the zygomatic arch, or above the hairline. Once again, undermining is not recommended within 1 cm of the location for receiving the bottom of the suture sling which will be described more fully below. As shown, the single elongate member 51 of the fixture 50 is inserted into the incision 140, to a depth of penetration which brings the eyelet 55 of the elongate member 51 into alignment with the location for the bottom of the suture sling which is to be formed, at a position along the centerline 21 which extends through the aperture 56 of the guide 54, as previously described, and the guide 54 is positioned over the patient's skin.

The fixture 50 will then be ready to receive an appropriate suture, as previously described (either with or without the use of a cannula 20), for continuing with the procedure to be performed. While a conventional suture (with or without a needle) can be used with the fixture 50, the fixture 50 is preferably used with the suture 65 shown in FIG. 13. Such a suture preferably includes two thickened sections 63, and a pair of knots associated with the center section 66, for locating the center point between the thickened sections 63. As an alternative, a single knot located at the center point 67 between the thickened sections 63, as shown in FIG. 13, can be used for this.

Referring to FIG. 46, the cannula 20 is inserted into the aperture 56 formed in the guide 54 of the fixture 50, passing through the aperture 56 of the guide 54, through the puncture 126 for entering the skin, through the eyelet 55 of the elongate member 51, and through the puncture 127 for exiting the skin. A spatula, or the tool 100 shown in FIG. 20, can be used to depress the skin at the exit puncture 127. The handle 52 of the fixture 50 can also be provided with a guard similar to the guard 15 of the fixture 1, if desired. The selected suture (for example, the illustrated suture 65) can then be threaded through the cannula 20 so that the thickened sections 63 extend from the punctures 126, 127, and so that the center section 66 is located within the subcutaneous tissue, adjacent to the eyelet 55 associated with the elongate member 51.

Figure 47:
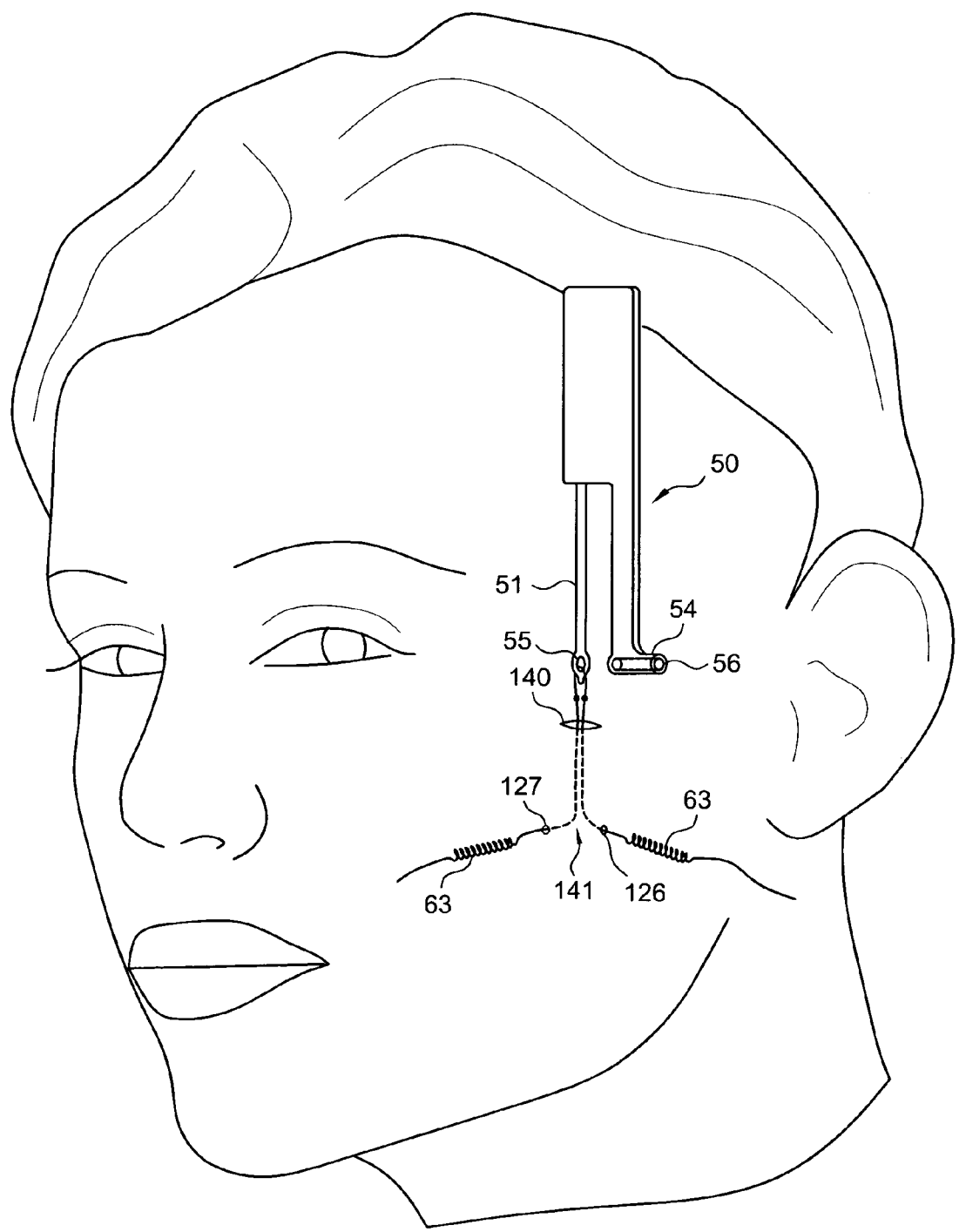

Referring to FIG. 47, the elongate member 51 is then withdrawn from the incision 140, in turn drawing the center section 66 of the suture 65 through the incision 140. Continued withdrawal of the elongate member 51 causes the thickened sections 63 to approach the skin at the punctures 126, 127.

Figure 48:
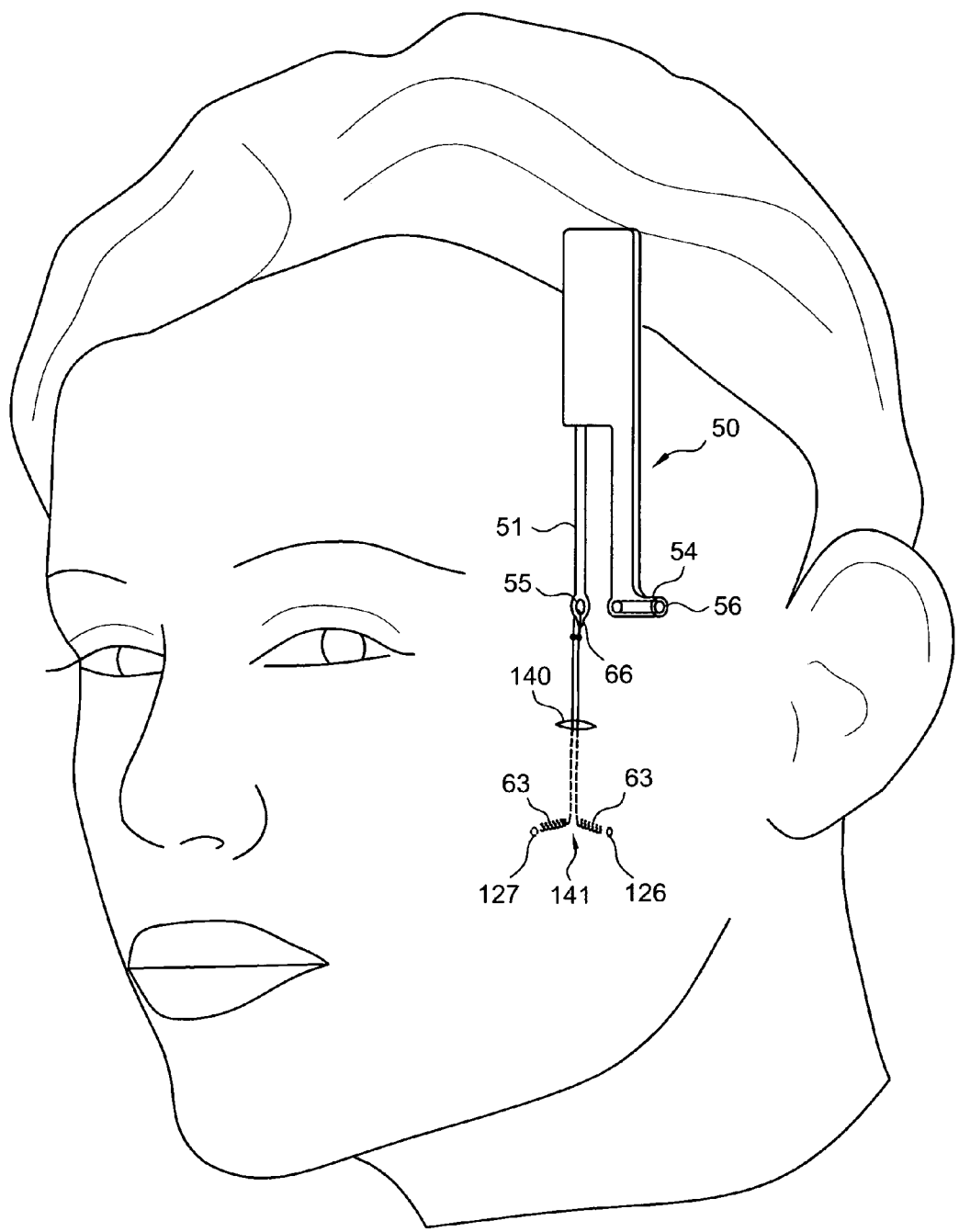

Referring to FIG. 48, further withdrawal of the elongate member 51 draws the thickened sections 63 of the suture 65 through the punctures 126, 127. When the elongate member 51 has been fully extracted, the thickened sections 63 of the suture 65 will be drawn together at a junction point 141 which is located at the subcutaneous termination of the penetration of the elongate member 51. To ensure that the thickened sections 63 are positioned together, the knot or knots of the center section 66 can be observed, on either side of the eyelet 55, as the elongate member 51 is fully withdrawn from the incision 140. Suitable adjustments can be made during withdrawal of the elongate member 51 to correct this spacing and make the ends of the suture 65 equidistant.

Figure 49:
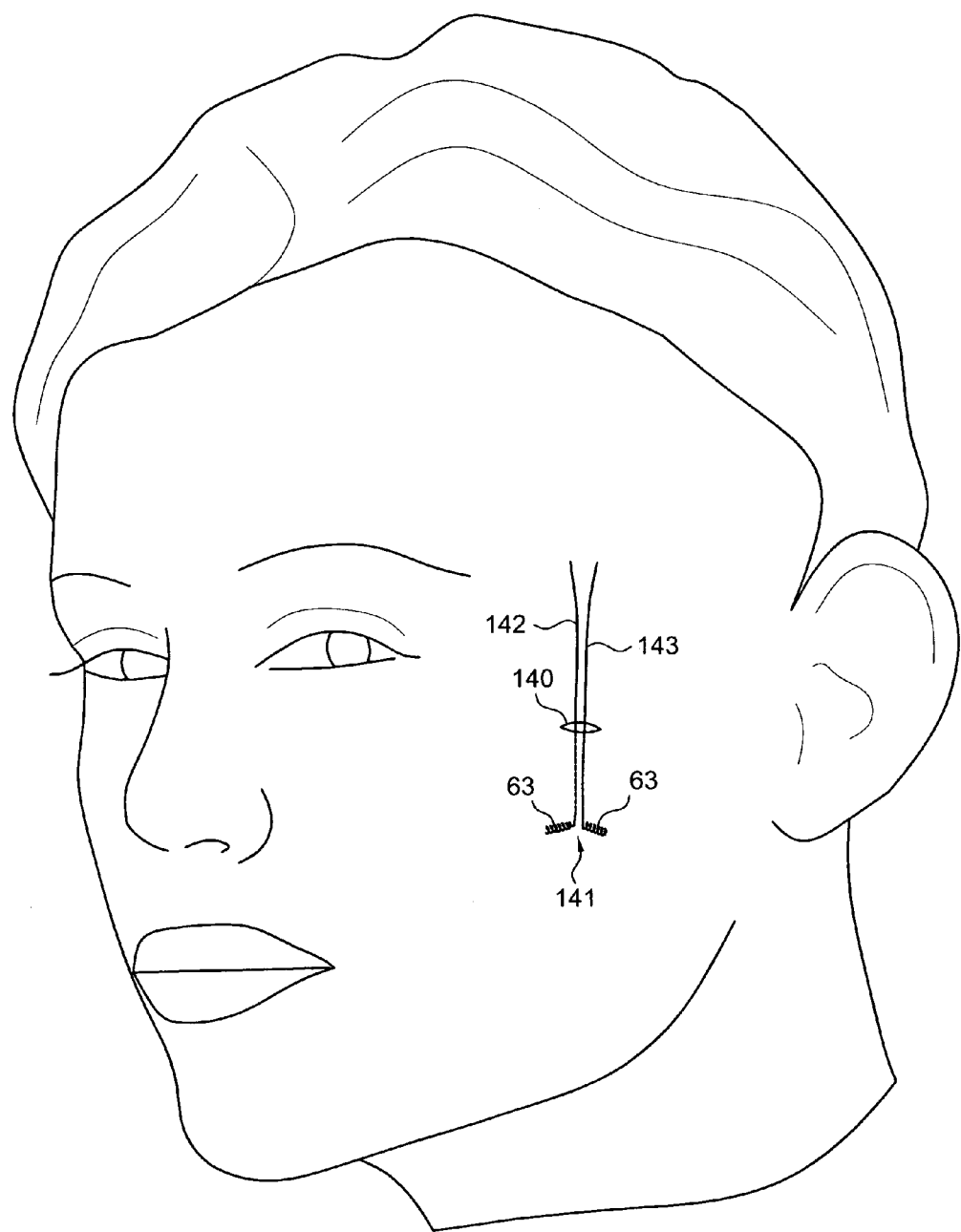

Referring to FIG. 49, the exposed center section 66 of the suture 65 is cut from the eyelet 55, at the top of the loop, creating ends 142, 143 substantially corresponding to the ends 131, 132 of the suture 130 previously described. As a result, the ends 142, 143 of the suture 65 will extend from the incision 140, and the thickened sections 63 of the suture 65 will remain anchored in the subcutaneous tissue. The resulting sling is then tensioned to lift the tissue, and is then anchored, as previously described, to complete the desired surgical procedure. Under tension, the pair of thickened sections 63 are prevented from passing up the channel which was developed by the elongate member 51, when inserted into the incision 140, because the combined size of the two thickened sections 63 is too large to fit within the channel.

Figure 50:
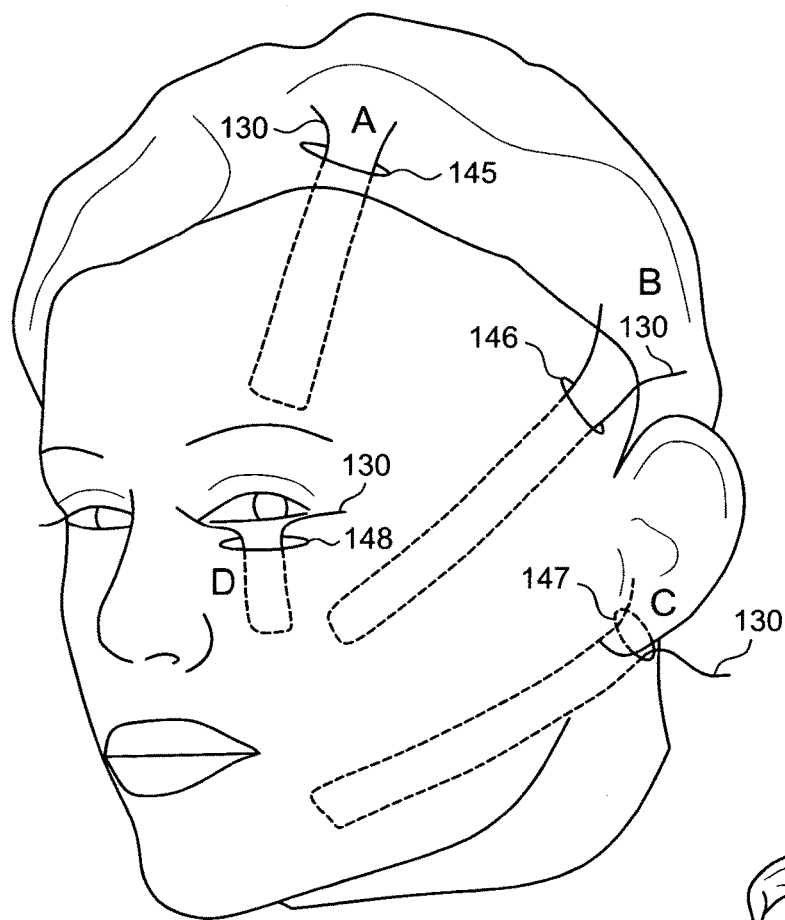
FIGS. 50 and 51 are illustrations showing various surgical procedures which can be performed in accordance with the present invention.
Figure 51:
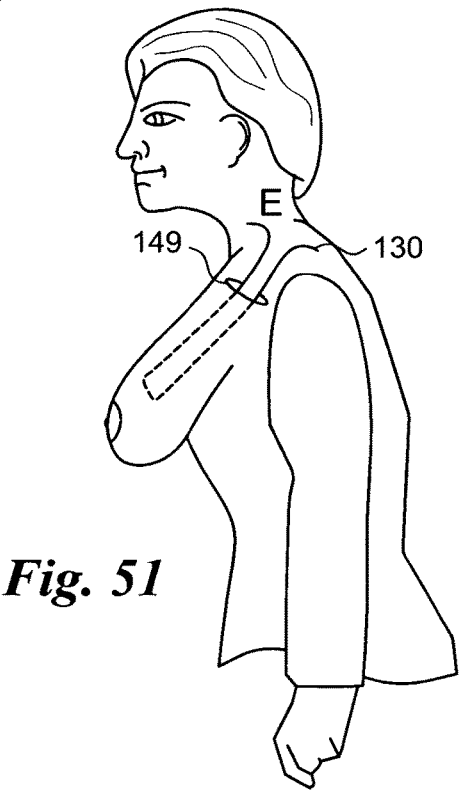

FIG. 50 shows examples of some of the variety of other surgical procedures which can be performed using the above-described apparatus. The placement of a suture sling 135 for performing a brow lift is shown in the region A, in combination with an entrance location 145. The placement of a suture sling 135 for performing a mid face lift is shown in the region B, in combination with an entrance location 146. The placement of a suture sling 135 for performing a chin lift is shown in the region C, in combination with an entrance location 147. The placement of a suture sling 135 for performing an under-eye lift is shown in the region D, in combination with an entrance location 148. FIG. 51 shows the placement of a suture sling 135 for performing a breast lift, in the region E, in combination with an entrance location 149.

For purposes of performing an under-eye lift, the fixture 1, 30, 35, 50 selected for use should have elongate members which are shortened, or in the alternative, curved or bent, as shown in FIG. 7, so the selected apparatus can fit into the relatively small spaces available. For purposes of performing a brow lift, the selected fixture should have a curved or bent body, as shown in FIG. 8, so the selected apparatus can extend over the forehead of the patient.

As a further alternative, and for any of the various surgical procedures which can be performed using the fixtures 1, 30, 50, one or more of the elongate members 6, 7, 51 can be replaced with the tool 105 of FIGS. 21 and 22. In such cases, the portion 110 of the wire 107 can be selectively deployed from the opening 109, developing an eyelet which is expandable and closable, for replacing the fixed eyelets 8, 9, 55. The remainder of the procedure to be performed will proceed in substantially similar manner, as previously described, using the expandable portion 110 of the tool 105 to receive the suture 130, either with or without the assistance of the cannula 20, and to close down on the suture 130 to facilitate extraction of the positioned suture 130. The tool 105 can also serve as an alternative to use of the undermining tools 75, 80, if desired.

The entrance locations 145, 146, 147, 148, 149, respectively, of the foregoing lifts are typical, and can permit longer incisions because they are located in hidden places, such as above the hair line, or in the breast. By comparison, the previously discussed entrance incisions 115, 116 are preferably tiny incisions to avoid scar tissue in a noticeable place. Also, the anchoring procedures used in these locations can be different from the above-described procedures. The anchoring procedure used can be varied, as appropriate, and can include the use of a bone penetration channel, staples, screws, a ligament, a muscle or the like. Typically, the incisions produced are closed by thin clear dissolving sutures, or some other similar technique.

It will therefore be understood that while the present invention has been described based on specific embodiments incorporating specified parts, the present invention further encompasses all technical equivalents of the parts described, and that various changes in the details, materials, arrangement and combination of parts which have been herein described and illustrated in order to explain the nature of this invention may be made by those skilled in the art within the principle and scope of the invention as expressed in the following claims.

What is claimed is:

1. An apparatus for remotely and subcutaneously positioning a suture in tissue, the apparatus comprising:
    a first body, at least one elongate member extending from the first body, and at least two eyelets for engaging the suture, each of the at least one elongate member having one or more of the at least two eyelets at a distal end thereof, the at least two eyelets defining a common longitudinal axis extending therethrough and each eyelet defining a respective length thereof in a dimension parallel to the longitudinal axis, and
    a second body movably attached to the first body, the second body having a guide arm extending therefrom, the guide arm including a keying structure for aligning a suture passing instrument with the longitudinal axis extending through the at least two eyelets of the at least one elongate member, the keying structure defining a length thereof in a dimension parallel to the longitudinal axis and a width thereof in a dimension perpendicular to the longitudinal axis, the length of the keying structure being greater than the width thereof and the length of the keying structure being greater than each of the respective lengths of the at least two eyelets,
    wherein the first and second bodies are movable relative to each other between a first position, where the first and second bodies are separated apart such that the keying structure and the suture passing instrument are not aligned with the longitudinal axis extending through the at least two eyelets, and a second position, where the first and second bodies are closed together, the keying structure aligning the suture passing instrument with the longitudinal axis extending through the at least two eyelets,
    wherein the guide arm is spaced from the at least one elongate member in both the first and second positions, and
    wherein the keying structure directs the suture passing instrument along the longitudinal axis and through the at least two eyelets of the at least one elongate member when the apparatus is in the second position.

2. The apparatus of claim 1 wherein the keying structure of the guide arm defines a longitudinal axis extending therethrough, and wherein the longitudinal axis of the keying structure is aligned with the longitudinal axis of the at least two eyelets of the at least one elongate member in the second position.

3. The apparatus of claim 1 wherein the keying structure of the guide arm defines a longitudinal axis extending therethrough, and wherein the longitudinal axis of the keying structure is parallel to and spaced from the longitudinal axis of the at least two eyelets opening of the at least one elongate member in the second position.

4. The apparatus of claim 1 wherein the keying structure of the guide arm is an aperture including an extended passageway.

5. The apparatus of claim 1, in combination with the suture passing instrument, the suture passing instrument having a shaft portion for passing the suture, wherein portions of the suture passing instrument are slidingly received by the keying structure of the guide arm and in the at least two eyelets of the at least one elongate member.

6. The apparatus of claim 5 wherein the suture passing instrument is a cannula.

7. The apparatus of claim 1 wherein the distal end of the at least one elongate member further includes a pointed tip extending from the distal end.

8. The apparatus of claim 1 which further includes a guard extending from the second body.

9. The apparatus of claim 8 wherein the guard has an open region which is aligned with the longitudinal axis of the at least two eyelets.

10. The apparatus of claim 8 wherein the guard is spaced from the at least two eyelets.

11. The apparatus of claim 1 wherein the at least one elongate member comprises two, spaced elongate members.

12. The apparatus of claim 11 wherein each of the two elongate members has an eyelet of the at least two eyelets.

13. The apparatus of claim 11 further comprising a guard extending from the second body, wherein the guard is spaced from the at least two eyelets of the elongate members, and wherein the guard has an open region which is aligned with the longitudinal axis.

14. The apparatus of claim 1 wherein the second body is contiguous with the first body.

15. The apparatus of claim 14 wherein the guide arm aligns the suture passing instrument with the longitudinal axis when the first body and the second body are contiguous.

16. The apparatus of claim 14 wherein the first body and the second body are joined by a hinge located on portions of the first body and the second body which are opposite to the at least one elongate member and the guide arm.

17. The apparatus of claim 14 wherein the first body and the second body are connectable by a fastener extending therebetween.

18. The apparatus of claim 14 which further includes a guard extending from the second body, wherein the guard is spaced from the at least two eyelets of the at least one elongate member, and wherein the guard has an open region which is aligned with the axis of the at least two eyelets.

19. The apparatus of claim 14, in combination with the suture passing instrument, the suture passing instrument having a shaft portion for passing the suture, wherein the suture passing instrument is slidingly received by the keying structure of the guide arm and in the at least two eyelets of the at least one elongate member.

20. The apparatus of claim 1 wherein the at least two eyelets are expandable and closable over the suture.

21. The apparatus of claim 20 wherein the at least one elongate member is a cannula having an aperture formed in side portions of the cannula, in combination with a wire extending through the cannula and past the aperture, and wherein the wire has an end fixed to an end of the cannula.

* * * * *